(12) United States Patent
Anderson et al.

(10) Patent No.: US 11,452,479 B2
(45) Date of Patent: Sep. 27, 2022

(54) SYSTEM AND METHOD FOR DIAGNOSING SOFT TISSUE CONDITIONS

(71) Applicant: The General Hospital Corporation, Boston, MA (US)

(72) Inventors: Richard R. Anderson, Boston, MA (US); Adam B. Raff, Boston, MA (US); William A. Farinelli, Danvers, MA (US); Daniela Kroshinsky, Boston, MA (US); Antonio Ortega-Martinez, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 297 days.

(21) Appl. No.: 16/500,462

(22) PCT Filed: Apr. 5, 2018

(86) PCT No.: PCT/US2018/026280
§ 371 (c)(1),
(2) Date: Oct. 3, 2019

(87) PCT Pub. No.: WO2018/187586
PCT Pub. Date: Oct. 11, 2018

(65) Prior Publication Data
US 2020/0121243 A1 Apr. 23, 2020

Related U.S. Application Data

(60) Provisional application No. 62/562,533, filed on Sep. 25, 2017, provisional application No. 62/504,135, (Continued)

(51) Int. Cl.
*A61B 5/00* (2006.01)
*A61B 5/01* (2006.01)
*G06T 7/00* (2017.01)

(52) U.S. Cl.
CPC ............ *A61B 5/441* (2013.01); *A61B 5/0075* (2013.01); *A61B 5/01* (2013.01); *A61B 5/7264* (2013.01);
(Continued)

(58) Field of Classification Search
CPC .............................. A61B 5/0059; A61B 5/445
(Continued)

(56) References Cited

U.S. PATENT DOCUMENTS

| 2006/0084864 A1* | 4/2006 | Schmitt | A61B 5/0053 600/431 |
| 2009/0318815 A1* | 12/2009 | Barnes | A61B 5/0064 600/473 |

(Continued)

OTHER PUBLICATIONS

Arakaki, R. Y., et al. The Impact of Dermatology Consultation on Diagnostic Accuracy and Antibiotic Use Among Patients With Suspected Cellulitis Seen at Outpatient Internal Medicine Offices: A Randomized Clinical Trial. JAMA Dermatol. 150, 1056-1061 (2014).

(Continued)

*Primary Examiner* — Fabricio R Murillo Garcia
(74) *Attorney, Agent, or Firm* — Quarles & Brady LLP

(57) ABSTRACT

A diagnostic system is provided for classifying a soft tissue condition within a region of interest of a subject. The diagnostic system comprises a spectrometer system configured to irradiate a soft tissue within a region of interest of a subject, and configured to generate spectral data by acquiring at least a portion of the reflected or emitted light from the region of interest. The diagnostic system further comprises a thermal detection system including at least one thermal sensor that is configured to acquire thermal detection data from the region of interest. A computer system is then used to build a classification model based on input thermal detection and spectral data. The classification model is then (Continued)

applied to an unknown soft tissue condition to classify the condition (e.g., classifying cellulitis from pseudocellulitis).

19 Claims, 26 Drawing Sheets

Related U.S. Application Data filed on May 10, 2017, provisional application No. 62/481,886, filed on Apr. 5, 2017.

(52) U.S. Cl.
CPC .... *G06T 7/0012* (2013.01); *A61B 2562/0271* (2013.01); *G06T 2207/20084* (2013.01); *G06T 2207/20104* (2013.01); *G06T 2207/30088* (2013.01)

(58) Field of Classification Search
USPC .......................................................... 600/306
See application file for complete search history.

(56) References Cited

U.S. PATENT DOCUMENTS

| | | | | |
|---|---|---|---|---|
| 2013/0114868 | A1* | 5/2013 | Burlina | A61B 5/444 382/128 |
| 2016/0045114 | A1 | 2/2016 | Dacosta et al. | |
| 2018/0025303 | A1* | 1/2018 | Janz | G16H 50/20 705/2 |

OTHER PUBLICATIONS

Brown JQ, et al. Quantitative Optical Spectroscopy: A Robust Tool for Direct Measurement of Breast Cancer Vascular Oxygenation and Total Hemoglobin Content In vivo. Cancer Res. 2009;69(7):2919-26.

Christensen, K. L. Y. et al. Infectious Disease Hospitalizations in the United States. Clin. Infect. Dis. 49, 1025-1035 (2009).

David, C. V. et al. Diagnostic accuracy in patients admitted to hospitals with cellulitis. Dermatol. Online J. 17, (2011).

Fujita, K., et al. Usefulness of infrared Thermal Imaging Camera for Screening of Postoperative Surgical Site Infection after the Nuss Procedure. Case Rep. Surg. 2013, e946156 (2013).

Harris, P.A. et al. Research Electronic Data Capture (REDCap)—A metadata-driven methodology and workflow process for providing translational research informatics support. J. Biomed. Inform. 42, 377-381 (2009).

International Searching Authority, International Search Report and Written Opinion for application PCT/US2018/026280, dated Jun. 28, 2018.

Jain, S. R. et al. Infectious diseases specialist management improves outcomes for outpatients diagnosed with cellulitis in the emergency department: a double cohort study. Diagn. Microbial. Infect. Dis. 81, 371-375 (2017).

Jenkins, T. C. et al. Skin and soft-tissue infections requiring hospitalization at an academic medical center: opportunities for antimicrobial stewardship. Clin. Infect. Dis. Off Pub!. Infect. Dis. Soc. Am. 51, 895-903 (2010).

Kaye, K. S. et al. Rising United States Hospital Admissions for Acute Bacterial Skin and Skin Structure Infections: Recent Trends and Economic Impact. PLoS One 10, (2015).

Khachatryan A, et al. Skin and skin structure infections (SSSIs) int he emergency department (ED): Who gets admitted? Society for Academic Emergency Medicine Annual Meeting. Dallas, TX; 2014.

Kimball AB, et al. The US dermatology workforce: A specialty remains in shortage. J. Am. Acad. Dermatol. 2008;59(5):741-5.

Ko LN, et al. "Skin surface temperatures measured by thermal imaging aid in the diagnosis of cellulitis." Journal of Investigative Dermatology 138.3 (2018): 520-526.

Kollias N, et al. A Single Parameter, Oxygenated Hemoglobin, Can Be Used to Quantify Experimental Irritant-Induced Inflammation. J. Invest. Dermatol. 1995;104(3):421-4.

Levell NJ, et al. Severe lower limb cellulitis is best diagnosed by dermatologists and managed with shared care between primary and secondary care. Br. J. Dermatol. 2011;164(6):1326-8.

Linden, A. Measuring diagnostic and predictive accuracy in disease management: an introduction to receiver operating characteristic (ROC) analysis. J. Eval. Clin. Pract. 12, 132-139 (2006).

Mallia RJ, et al. Oxygenated hemoglobin diffuse reflectance ratio for in vivo detection of oral pre-cancer. J. Biomed. Opt. 2008;13(4):041306.

McNamara DR, et al. A Predictive Model of Recurrent Lower Extremity Cellulitis in a Population-Based Cohort. Arch Intern Med. 2007;167(7):709-715. doi:10.1001/archinte.167.7.709.

McNamara, D. R., et al. "Incidence of lower-extremity cellulitis: a population-based study in Olmsted county, Minnesota." Mayo Clinic Proceedings. vol. 82. No. 7. Elsevier, 2007.

Miller, L. G. et al. Incidence of skin and soft tissue infections in ambulatory and inpatient settings, 2005-2010. BMC Infect. Dis. 15, (2015).

Montalto M, et al. Skin surface temperature: a possible new outcome measure for skin and soft tissue infection. Aust Fam Physician. 2013;42(9):653-657.

Pallin, D. J. et al. Increased US Emergency Department Visits for Skin and Soft Tissue Infections, and Changes in Antibiotic Choices, During the Emergence of Community-Associated Methicillin-Resistant *Staphylococcus aureus*. Ann. Emerg. Med. 51, 291-298 (2008).

Peterson RA, et al. Increasing Incidence, Cost, and Seasonality in Patients Hospitalized for Cellulitis. Open Forum Infect Dis. 2017;4(1). doi:10.1093/ofid/ofx008.

Raff AB, et al. A predictive model for diagnosis of lower extremity cellulitis: A cross-sectional study. J. Am. Acad. Dermatol. 2017;76(4):618-625.e2.

Raff AB, et al. Cellulitis: A review. JAMA. 2016;316(3):325-37.

Romano, C. L., et al. Telethermographic findings after uncomplicated and septic total knee replacement. The Knee 19, 193-197 (2012).

Strazzula, L. et al. Inpatient dermatology consultation aids diagnosis of cellulitis among hospitalized patients: A multi-institutional analysis. J Am. Acad. Dermatol. 73, 70-75 (2015).

Tay Ey, et al. Cellulitis Recurrence Score: a tool for predicting recurrence of lower limb cellulitis. J. Am. Acad. Dermatol. 2015;72(1):140-5.

The Dermatologist. The Growing Problem of Pseudocellulitis. [online] Published Nov. 21, 2014. [Retreived on Jun. 19, 2018 (Jun. 19, 2018)] Retrieved from the Internet URL:https://www.the-dermatologist.com/content/growing-problem-pseudocellulitis p. 1 and 2.

Walsh, T. L. et al. Appropriateness of antibiotic management of uncomplicated skin and soft tissue infections in hospitalized adult patients. BMC Infect. Dis. 16, 721 (2016).

Weng Qy, et al. Costs and Consequences Associated With Misdiagnosed Lower Extremity Cellulitis. JAMA Dermatol. Nov. 2016. doi:10.1001/jamadermatol.2016.3816.

Zakian CM, et al. In vivo quantification of gingival inflammation using spectral imaging. J. Biomed. Opt. 2008;13(5):054045.

\* cited by examiner

| Variable | Total (N=72) | | Pseudocellulitis (N=19) | | Cellulitis (N=53) | | P-Value |
|---|---|---|---|---|---|---|---|
| Age in years – median (IQR) | 58.7 | (44.5-73.9) | 69.8 | (59.5-76.7) | 54.2 | (39.8-68.1) | >0.01 |
| Gender – N (%) | | | | | | | 0.42 |
| Male | 43 | (59.7) | 10 | (52.6) | 33 | (62.3) | |
| Female | 29 | (40.3) | 9 | (47.4) | 20 | (37.7) | |
| Race – N (%) | | | | | | | 0.66 |
| White | 59 | (81.9) | 15 | (78.9) | 44 | (83.0) | |
| Asian or Pacific Islander | 4 | (5.6) | 2 | (10.5) | 2 | (3.8) | |
| American Indian | 0 | (0.0) | 0 | (0) | 0 | (0.0) | |
| Black | 3 | (4.2) | 1 | (5.3) | 2 | (3.8) | |
| Hispanic | 6 | (8.3) | 1 | (5.3) | 5 | (9.4) | |
| Cellulitis Risk Factors – N (%) | | | | | | | |
| Chronic Lymphedema | 12 | (16.7) | 3 | (15.8) | 9 | (17.0) | 0.92 |
| Tinea Pedis | 15 | (20.8) | 3 | (15.8) | 12 | (22.6) | 0.55 |
| Known Trauma | 23 | (31.9) | 3 | (15.8) | 20 | (37.7) | 0.07 |
| History of Skin Disease | 17 | (23.6) | 6 | (31.6) | 11 | (20.8) | 0.32 |
| Onychomycosis | 29 | (40.3) | 5 | (26.3) | 24 | (45.3) | 0.16 |
| Type II Diabetes | 17 | (23.6) | 5 | (26.3) | 12 | (22.6) | 0.72 |
| End Stage Renal Disease | 1 | (1.4) | 0 | (0) | 1 | (1.9) | 0.55 |
| Low-dose Immunosuppression | 2 | (2.8) | 0 | (0) | 2 | (3.8) | 0.4 |
| High-dose Immunosuppression | 1 | (1.4) | 1 | (5.3) | 0 | (0.0) | 0.09 |
| Active Cancer | 3 | (4.2) | 1 | (5.3) | 2 | (3.8) | 0.77 |

IQR: interquartile range

FIG. 19

| Variable | Total (N=72) | | Dermatology Consultation Cohort (N=40) | | Standard of Care Cohort (N=32) | | P-Value |
|---|---|---|---|---|---|---|---|
| Age in years - median (IQR) | 58.7 | (44.5-73.9) | 57.4 | (37.7-69.0) | 62.4 | (53.1 77.3) | 0.06 |
| Gender – N (%) | | | | | | | 0.73 |
| Male | 43 | (59.7) | 23 | (57.5) | 20 | (62.5) | |
| Female | 29 | (40.3) | 17 | (42.5) | 12 | (37.5) | |
| Race – N (%) | | | | | | | 0.36 |
| White | 59 | (81.9) | 31 | (77.5) | 28 | (87.5) | |
| Asian or Pacific Islander | 4 | (5.6) | 3 | (7.5) | 1 | (3.1) | |
| American Indian | 0 | (0.0) | 0 | (0) | 0 | (0) | |
| Black | 3 | (4.2) | 1 | (2.5) | 2 | (6.3) | |
| Hispanic | 6 | (8.3) | 5 | (12.5) | 1 | (3.1) | |

FIG. 20

| Alternative Diagnosis | Dermatology Consultation Cohort (n=11) | Standard of Care Cohort (n=8) |
|---|---|---|
| Abscess | n/a | 1 (12.5%) |
| Cryoglobinemia | 1 (9.1%) | n/a |
| Eczematous Dermatitis | 2 (18.1%) | n/a |
| Erythema Migrans | 1 (9%) | n/a |
| Erythema Nodosum | n/a | 1 (12.5%) |
| Flexor Tenosynovitis | 1 (9.1%) | n/a |
| Hematoma | 1 (9.1%) | n/a |
| Lymphedema | n/a | 2 (25%) |
| Venous Stasis Dermatitis | 4 (36.4%) | 3 (37.5%) |
| Vestibulitis | 1 (9.1%) | n/a |
| Wound | n/a | 1 (12.5%) |

FIG. 21

|  | Affected skin temperature (°C) | Unaffected skin temperature (°C) | Difference, mean (95% CI) p-value |
|---|---|---|---|
| Cellulitis, Mean (95% CI) | 34.1 (33.3 - 34.9) | 30.4 (29.2 - 31.6) | 3.7 (2.68 - 4.76) <0.00001 |
| Pseudocellulitis, mean (95% CI) | 31.5 (29.3 - 31.4) | 31.3 (25.1 - 37.1) | 0.2 (-1.07 - 1.49) 0.44425 |
| Difference, mean (95% CI) p-value | 2.6 (0.7 - 4.6) 0.008 | -0.9 (-3.3-1.6) 0.48 | 3.5 (1.9-5.2) 0.002 |

FIG. 22

| | Predictive Model:<br>Dermatology Consult Cohort<br>(Temperature Gradient ≥ 0.47°C) | Validation of Model:<br>Standard of Care Cohort<br>(Temperature Gradient ≥ 0.47°C) |
|---|---|---|
| Sensitivity | 96.6% | 100% |
| Specificity | 45.5% | 50% |
| Positive Predictive Value | 82.4% | 85.7% |
| Negative Predictive Value | 83.3% | 100% |
| Accuracy | 82.5% | 87.5% |

FIG. 23

|  | Predicted Cellulitis | Predicted Pseudocellulitis |  |
|---|---|---|---|
| Actual Cellulitis | 24 | 4 | 28 |
| Actual Pseudocellulitis | 0 | 4 | 4 |
| Totals | 24 | 8 | 32 |

FIG. 24

| Alternative Diagnosis | Dermatology Consultation Cohort (n=11) | Standard of Care Cohort (n=8) |
|---|---|---|
| Abscess | n/a | 1 (12.5%) |
| Cryoglobinemia | 1 (9.1%) | n/a |
| Eczematous Dermatitis | 2 (18.1%) | n/a |
| Erythema Migrans | 1 (9%) | n/a |
| Erythema Nodosum | n/a | 1 (12.5%) |
| Flexor Tenosynovitis | 1 (9.1%) | n/a |
| Hematoma | 1 (9.1%) | n/a |
| Lymphedema | n/a | 2 (25%) |
| Venous Stasis Dermatitis | 4 (36.4%) | 3 (37.5%) |
| Vestibulitis | 1 (9.1%) | n/a |
| Wound | n/a | 1 (12.5%) |

FIG. 25

|  | Model 1: Temperature Difference (Temperature Gradient ≥ 0.47°C) | Model 2: Percentage of affected skin temperature (Temperature Gradient ≥ 1.35% of affected skin temperature) |
|---|---|---|
| Equation | p=1/(1+exp(-(0.7089*x-0.3351))) | p = 1/(1+ exp(-(0.20264*x-0.27344))) |
| Sensitivity | 96.6% | 96.6% |
| Specificity | 45.5% | 45.5% |
| Positive Predictive Value | 82.4% | 82.4% |
| Negative Predictive Value | 83.3% | 83.3% |
| Accuracy | 82.5% | 82.5% |

FIG. 26

SYSTEM AND METHOD FOR DIAGNOSING SOFT TISSUE CONDITIONS

CROSS-REFERENCE TO RELATED APPLICATIONS

This application represents the national stage entry of PCT International Application No. PCT/US2018/026280 filed Apr. 5, 2018, which is based on, claims the benefit of, and incorporates herein by reference, U.S. Provisional Patent Application 62/481,886, filed Apr. 5, 2017, U.S. Provisional Patent Application 62/504,135, filed May 10, 2017, and U.S. Provisional Patent Application 62/562,533, filed Sep. 25, 2017.

STATEMENT REGARDING FEDERALLY SPONSORED RESEARCH

This invention was made with government support under T32 AR007098 awarded by the National Institutes of Health. The government has certain rights in the invention.

BACKGROUND

Cellulitis is a common skin and soft tissue infection (SSTI) that has been shown to be misdiagnosed over 30% of the time. This frequent misdiagnosis is due to the presence of many clinical mimics that possess similar signs and symptoms, collectively known as 'pseudocellulitis.' Annually, there are 2.3 million Emergency Department (ED) visits for cellulitis, with 17% of these visits resulting in admission to the hospital. As the number of hospitalizations from cellulitis has doubled from 1998, so has the total cost for cellulitis hospitalization to $3.74 billion annually. Cellulitis misdiagnosis in the hospital alone leads to an estimated 130,000 unnecessary admissions and $515 million in avoidable health care spending. Beyond cost, 92% of patients misdiagnosed with cellulitis in the hospital received unnecessary antibiotics, increasing their risk of antibiotic related complications such as anaphylaxis, drug rash, and *Clostridium difficile* infection.

While dermatology and infectious disease consultation is highly accurate in the diagnosis of cellulitis to the point of being considered the clinical gold standard diagnostic modality, specialty access remains limited. For example, the majority of cellulitis cases are not seen by a specialist but are managed exclusively by primary care, emergency medicine, or internal medicine physicians. In some instances, the physician may also suggest blood tests, a wound culture, or other laboratory tests to assist in making the diagnosis. However, the results for these tests may take up to one or two days, may be expensive, and do not always yield definitive results. The misdiagnosis rate of cellulitis remains high. This has led to rising healthcare costs attributed to, at least in part, unnecessary admission of patients into clinics and unnecessary administration of antibiotics and testing.

Currently, there is a need in the art for the development of diagnostic tools that can assist clinicians to differentiate cellulitis from other 'pseudocellulitis' conditions that present similar symptoms. The development of such tools would decrease the misdiagnosis rate, prevent unnecessary hospitalizations and complications, reduce overuse of antibiotics, and testing, and save money in healthcare spending.

SUMMARY OF THE DISCLOSURE

The present disclosure provides systems and methods for overcoming the aforementioned drawbacks by providing a diagnostic system that classifies, or provides information that assists a physician in diagnosing or classifying, soft tissue conditions in a region of interest of a subject. The diagnostic system of the present disclosure allows for quick and easy measurements that may, in some aspects, be acquired using an attachment on a mobile device. The diagnostic system presented herein can reduce the misdiagnosis rate of soft tissue conditions, such as classifying cellulitis from pseudocellulitis, and thereby preventing unnecessary hospitalizations, reducing overuse of antibiotics, and reduce overall healthcare spending.

In accordance with one aspect of the present disclosure, a diagnostic system is provided that includes a spectrometer system and a thermal detection system. The spectrometer system is configured to irradiate a soft tissue within a region of interest of a subject, and is further configured to generate spectral data by acquiring at least a portion of the reflected or emitted light from the region of interest. The thermal detection system includes at least one thermal sensor that is configured to acquire thermal detection data from the region of interest. The diagnostic system further includes a computer system communicatively coupled to the thermal detection system and the spectrometer system, where the computer system is programmed to: control the spectrometer system to generate the spectral data by irradiating the region of interest at one or more wavelength, and by acquiring at least a portion of light reflected or emitted from the region of interest; control the thermal detection system to acquire the thermal detection data from the region of interest using the at least one thermal sensor; utilize one or more parameter from the thermal detection data and the spectral data in a classification model that classifies the soft tissue in the region of interest as corresponding to a soft tissue infection; and generate a report that includes a classification of the soft tissue infection or a plurality of parameters indicative of the soft tissue infection.

In another aspect of the present disclosure, a diagnostic system is provided that includes a spectrometer system. The spectrometer system comprises a light source and a detector. The light source is configured to irradiate a soft tissue within a region of interest of a subject, and the detector is configured to acquire at least a portion of the reflected or emitted light from the region of interest. The detector may comprise a fiber optic probe communicatively coupled to a spectrometer, the fiber optic probe may include at least one illumination fiber configured to irradiate a soft tissue within a region of interest of a subject, and wherein the fiber optic probe further includes at least one detection fiber configured to generate spectral data by acquiring reflected irradiation from the region of interest. The diagnostic system further includes a computer system communicatively coupled to the spectrometer system, and where the computer system is programmed to: control the spectrometer system to generate the spectral data by irradiating the region of interest at one or more wavelength, and acquiring the reflected or emitted irradiation from the region of interest; utilize one or more parameter from the spectral data in a classification model that classifies the soft tissue in the region of interest as corresponding to a soft tissue infection; and generate a report that includes a classification of the soft tissue infection or a plurality of parameters indicative of the soft tissue infection.

In one aspect of the present disclosure, a diagnostic system is provided that includes a thermal detection system. The thermal detection system includes at least one thermal sensor that is configured to acquire thermal detection data from the region of interest. The diagnostic system further includes a computer system communicatively coupled to the thermal detection system, and where the computer system is programmed to: control the thermal detection system to acquire the thermal detection data from the region of interest using the at least one thermal sensor; and utilize one or more parameter from the thermal detection data in a classification model to differentiate cellulitis and pseudocellulitis; and generate a report that includes a classification of cellulitis or pseudocellulitis or a plurality of parameters indicative of cellulitis or pseudocellulitis.

In another aspect of the present disclosure, a diagnostic system is provided that includes a spectrometer system and a thermal imaging system. The spectrometer system is configured to irradiate a soft tissue within a region of interest of a subject, and is further configured to generate spectral data by acquiring reflected irradiation from the region of interest. The thermal detection system includes at least one thermal sensor that is configured to acquire thermal detection data from the region of interest. The diagnostic system further includes a computer system communicatively coupled to the thermal detection system and the spectrometer system, and wherein the computer system is programmed to: control the spectrometer system to generate the spectral data by irradiating the region of interest at one or more wavelength, and acquiring at least a portion of light reflected or emitted from the region of interest; control the thermal detection system to acquire the thermal detection data from the region of interest using the at least one thermal sensor; and generate at least one image of a soft tissue within the region of interest of the subject based on the thermal detection data and the spectral data.

In one aspect of the present disclosure, a method is provided for classifying a soft tissue condition in a region of interest of a subject. The method includes acquiring thermal detection data from a soft tissue in a region of interest in a subject using a thermal detection system. The method further includes acquiring spectral data by irradiating the soft tissue and acquiring at least a portion of the reflected or emitted light from the region of interest using a spectrometer system. One or more parameter from the thermal detection data and the spectral data is then generated using a computer system utilized in a classification model to classify the soft tissue in the region of interest as corresponding to a soft tissue infection. A report is then generated using the computer system that includes a classification of the soft tissue infection or a plurality of parameters indicative of the soft tissue infection.

In another aspect of the present disclosure, a method for classifying a soft tissue condition in a region of interest of a subject is provided. The method includes generating spectral data by irradiating a soft tissue in a region of interest of a subject and acquiring at least a portion of the reflected or emitted light from the region of interest using a spectrometer system. One or more parameter is then generated from the spectral data using a computer system, and the one or more parameter is then utilized in a classification model that classifies the soft tissue in the region of interest as corresponding to a soft tissue infection. The method further includes generating a report that includes a classification of the soft tissue infection or a plurality of parameters indicative of the soft tissue infection using the computer system.

In one aspect of the present disclosure, a method for classifying a soft tissue condition in a region of interest of a subject is provided. The method includes acquiring thermal detection data from skin in a region of interest of a subject using a thermal detection system. One or more parameter from the thermal detection data is generated using a computer system and utilized in a classification model to differentiate the soft tissue in the region of interest between cellulitis and pseudocellulitis. The computer system is then utilized to generate a report that includes a classification of cellulitis or pseudocellulitis or a plurality of parameters indicative of cellulitis or pseudocellulitis.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

The present invention will hereafter be described with reference to the accompanying drawings, wherein like reference numerals denote like elements.

FIG. 19 is table illustrating baseline patient demographics, comparing patients with diagnoses of cellulitis and pseudocellulitis.

FIG. 20 is table illustrating baseline patient demographics, comparing the cohorts randomized to dermatology consultation vs. standard of care.

FIG. 21 is a table illustrating alternative diagnoses (aka pseudocellulitis) of patients randomized to both dermatology consultation and standard care.

FIG. 22 is a table comparing the average affected skin temperatures, unaffected skin temperatures, and temperature differences in patients with cellulitis and pseudocellulitis among those randomized to dermatology consultation.

FIG. 23 is a table comparing two classification models. Sensitivity, specificity, positive and negative predictive value, and accuracy of model in dermatology and standard of care cohort. $p=1/(1+\exp(-(0.7089*x-0.3351\}))\}$, x=temperature gradient or percentage, p=probability of cellulitis.

FIG. 24 is a table showing a confusion matrix for the classification model presented in FIG. 17. The confusion matrix demonstrates the use of the classification model from FIG. 17 in correctly predicting diagnoses in the cohort randomized to standard of care.

FIG. 25 is a table illustrating alternative diagnoses, also known as pseudocellulitis, of patients randomized to both dermatology consultation and standard of care.

FIG. 26 is a table comparing the two classification models presented in FIG. 17 and FIG. 18. Sensitivity, specificity, positive and negative predictive value, and accuracy of the classification models is illustrated in a cohort seen by dermatology consultation; x=temperature gradient or percentage; p=probability of cellulitis.

DETAILED DESCRIPTION

Figure 1:
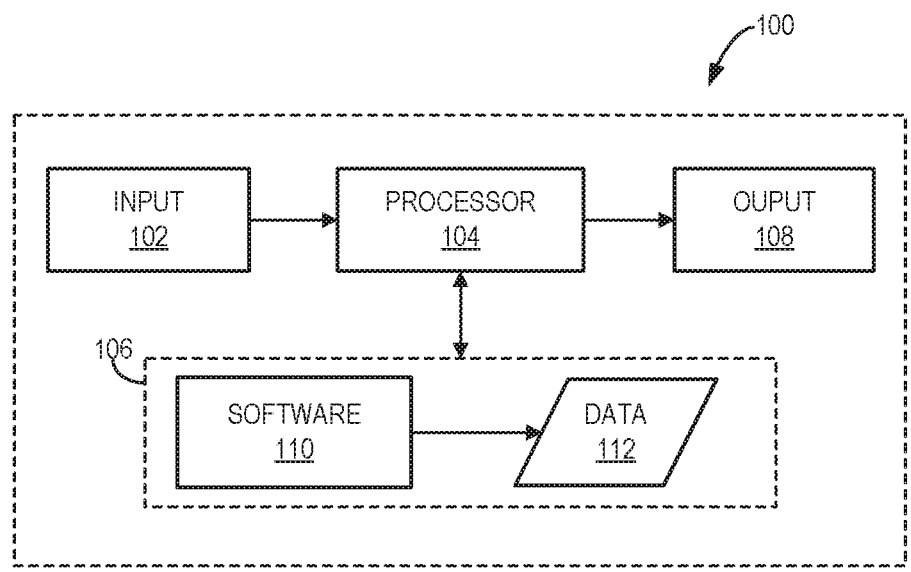
FIG. 1 is a block diagram illustrating an example of a system in accordance with one aspect of the present disclosure.

Referring to FIG. 1, a block diagram of an example computer system 100 that can be used to classify a soft tissue condition from a region of interest of a subject is illustrated. The computer system 100 generally includes an input 102, at least one processor 104, a memory 106, an output 108, and any device for reading computer-readable media (not shown). The computer system 100 may be, for example, a workstation, a mobile device, a laptop computer, a personal digital assistant (PDA), a multimedia device, a network server, a mainframe, a spectrometer system, a thermal detection system, or any other general-purpose or application-specific computing device, or a system in communication with or part of a diagnostic system, as will be described in FIG. 2. The computer system 100 may operate autonomously or semi-autonomously, or may read executable software instructions from a computer-readable medium (such as a hard drive, a CD-ROM, flash memory and the like), or may receive instructions from a user, or any other source logically connected to a computer or device, such as another networked computer or server, via the input 102.

The input 102 may take any shape or form, as desired, for operation of the computer system 100, including the ability for selecting, entering, or otherwise specifying parameters consistent with operating the computer system 100. In some aspects, the input 102 may be configured to receive data, such as thermal detection data acquired with a thermal detection system, which may include a thermal imaging camera or thermal probe and/or spectral data acquired with a spectrometer system. The input 102 may also be configured to receive other data or information that is considered useful in assisting the system to classify the soft tissue condition of the subject. In one aspect, the input 102 data to the computer system 100 may include clinical characteristics of the patient, such as the patient's age, heart rate, white blood cell (WBC) count, and any data collected during a physical examination.

Among the processing tasks for operating the computer system 100, the at least one processor 104 may also be configured to receive data, such as spectral and/or thermal detection data, wherein the data may be pre-processed, and/or may undergo any number of further processing steps using the at least one processor 104. In some aspects, the at least one processor 104 may be capable of performing computations using signals derived from spectral data and/or thermal detection data. For example, the at least one processor 104 may be capable executing appropriate instructions, such as instructions provided by software 110 from the memory 106. The data may be provided to the processor 104 from stored data 112 in the memory 106.

In some aspects, the processor 104 performs computations using instructions received from the software 110 to generate an output 108. The output 108 may take any shape or form, as desired, and may be configured for displaying any information in relation to the spectral and/or thermal detection data. In some aspects, the output 108 may be configured in the form of a report that classifies the soft tissue condition, or provides information to a physician to assist in diagnosing, in the region of interest of the subject. The report may be generated based on input spectral and/or thermal detection data provided to the processor 104 of the computer system 100. Example soft tissue conditions that the computer system 100 may classify include, but are not limited to, soft tissue infections, skin and soft tissue infections, such as classifying cellulitis or pseudocellulitis from the region of interest of the subject.

Figure 2:
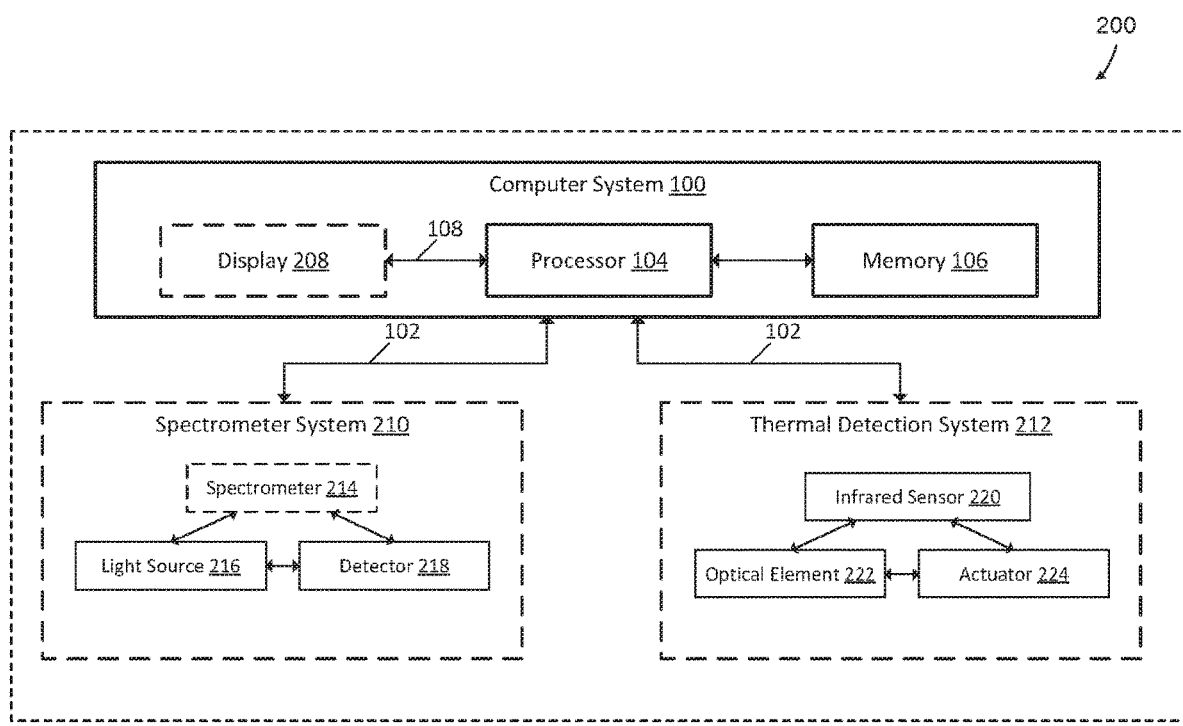
FIG. 2 is a block diagram of a diagnostic system in accordance with another aspect of the present disclosure.

Referring particularly now to FIG. 2, a block diagram of an example diagnostic system 200 that can be used to classify a soft tissue condition within a region of interest of a subject is illustrated. The diagnostic system 200 includes the same or similar components as described with respect to FIG. 1. For example, the diagnostic system 200 generally includes at least one processor 104 that includes a commercially available programmable machine running on a commercially available operating system. The at least one processor 104 is configured to execute instructions, such as software instructions provided in the memory 106. An optional display 208 may be included in the diagnostic system 200, which may further include one or more input device, such as a keyboard and mouse or touch-screen. The display 208 may provide an operator interface that enables operational parameters to be entered into the diagnostic system 200. The display 208 may also be configured to display the output 108 generated from the at least one processor 104.

In general, the computer system 100 may be communicatively coupled to at least one other system (indicated by dotted lines in FIG. 2), such as a spectrometer system 210 and/or a thermal detection system 212, which may include a thermal sensor. The computer system 100 may be connected via an input 102, which may include any suitable communicative connection, whether wired, wireless, or a combination of both, such that the computer system 100 may receive and send information with the spectrometer system 210 and the thermal detection system 212.

The spectrometer system 210 functions in response to instructions downloaded from the computer system 100 to operate the spectrometer system 210 to generate and acquire spectral data from a soft tissue in a region of interest. In general, the spectrometer system 210 typically includes an optional spectrometer 214 for receiving and processing signals, a light source 216, and a detector 218. The spectrometer system 210 may generate the spectral data by irradiating the soft tissue with one or more wavelength using the light source 216, and may acquire the spectral data by detecting at least a portion of the reflected or emitted light using the detector 218. The light source 216 may be selected from a number of suitable light sources, such as a broad band light source, a UV light source, a UV-Vis-NIR light source, a VIS and NIR light source, one or more light-emitting diode (LED), and a white light LED, such as the light source in a smartphone or mobile device. In one aspect, the detector 218 comprises a fiber optic probe that is configured with one or more illumination fiber that transfers irradiation from the light source 216 to the soft tissue in the region of interest. The fiber optic probe may further include at least one detection fiber that transfers at least a portion of light that is reflected or emitted from the region of interest to the detector 218. The reflected or emitted signals are then transferred to the spectrometer 214 and/or the computer system 100 to generate spectral data. In one aspect, the detector 218 may comprise the camera configured within a smartphone or mobile device, and the light source may comprise a white light LED configured within the smartphone or mobile device.

In one aspect, the spectrometer system 210 comprises a diffuse reflectance spectrometer that generates a diffuse reflectance spectrum from the soft tissue in the region of interest. Diffuse reflectance measurements are typically acquired using an irradiation between 400 to 900 nm. The diffuse spectrum includes the absorption and scattering properties of a target soft tissue, where an absorption coefficient may be used to determine one or more physiological parameters from the region of interest, such as blood oxygenation levels by taking a ratio of the oxygenated and deoxygenated hemoglobin peaks (542 nm and 556 nm, respectively). Other suitable physiological parameters may include a capillary refill time based on the spectral data. In other aspects, the spectrometer system 210 may comprise a fluorescence spectrometer that is configured to acquire light emitted from the region of interest, typically visible light. Fluorescence spectroscopy typically occurs at a wavelength between 300 to 460 nm, where emission may be measured up to 600 nm.

The spectral data generated by the spectrometer system 210 may then be provided as an input 102 to the processor 104 in the computer system 100. The computer system 100 may then be programmed to process the spectral data to generate and display a spectrum or spectra of the soft tissue. As will be described in more detail, the computer system 100 may also generate a report that classifies a soft tissue condition within the region of interest (e.g., as cellulitis or pseudocellulitis), or provides information that assists a physician in diagnosing the soft tissue condition, based on the spectral data. In one aspect, the soft tissue condition is located on an external soft tissue (e.g., skin), and may comprise a skin and soft tissue infection. In one non-limiting example, the soft tissue condition comprises cellulitis or pseudocellulitis.

The thermal detection system 212 functions in response to instructions downloaded from the computer system 100 to operate the thermal detection system 212 to acquire thermal detection data from the soft tissue in the region of interest. In general, the thermal detection system includes one or more thermal sensor 220, an optical element 222, and an actuator 224. In one aspect, the one or more thermal sensor 220 may be configured to acquire thermal detection data by detecting infrared radiation from the soft tissue in the region of interest. For example, the one or more thermal sensor 220 may be configured to detect, for example, mid wave infrared wave bands (MWIR), long wave infrared wave bands (LWIR), and/or other imaging bands as desired. Suitable sensors may include focal plane arrays such as microbolometers.

The thermal detection system 212 may include one or more actuator 224 which may be used to adjust the focus of the acquired thermal detection data and/or thermal image. For example, the one or more actuator 224 may move optical element 222, the one or more thermal sensor 220, and other components to focus and defocus the thermal detection data or image, as desired. The thermal detection data may be used to produce one or more physiological parameters from the region of interest. In one aspect, the thermal detection system 212 may detect temperature measurements between 20° C. and 120° C. without contacting the soft tissue.

The thermal detection data generated by the thermal detection system 212 may then be provided as an input 102 to the processor 104 in the computer system 100. The computer system 100 may then be programmed to process the thermal detection data to generate and display a thermal image of the soft tissue. As will be described in more detail, the computer system 100 may also generate a report that classifies a soft tissue condition within the region of interest (e.g., as cellulitis or pseudocellulitis), or provides information that assists a physician in diagnosing the soft tissue condition, based on the thermal detection data. In one aspect, the soft tissue condition comprises an external soft tissue, such as a skin and soft tissue infection. In one non-limiting example, the soft tissue condition comprises cellulitis or pseudocellulitis.

In one aspect, both the thermal detection data generated by the thermal detection system 212 and spectral data generated by the spectrometer system 210 may be provided as inputs 102 to the processor 104 in the computer system 100. In another aspect, the computer system 100 may then be programmed to process both the thermal detection data and the spectral data to generate a report that classifies soft tissue condition within the region of interest (e.g., as cellulitis or pseudocellulitis), or provides information that assists a physician in diagnosing the soft tissue condition. In one aspect, the soft tissue condition comprises an external soft tissue, such as a skin and soft tissue infection. In one non-limiting example, the soft tissue condition comprises cellulitis or pseudocellulitis. Additionally, the computer system 100 may then be programmed to process both the thermal detection data and the spectral data to generate at least one image or spectrum based on the soft tissue in the region of interest.

As described, the misdiagnosis rate of soft tissue conditions, such as cellulitis or pseudocellulitis, remains high. This has led to rising healthcare costs attributed to, at least in part, unnecessary admission of patients into clinics and unnecessary administration of antibiotics. The diagnostic system 200 offers advantages over conventional techniques, which typically rely on a diagnosis from a specialist, such as a dermatologist. For example, the diagnostic system 200 uses easy to measure parameters that produce a classification of the soft tissue in the region of interest, which may be used as tool to assist physicians in diagnosing soft tissue conditions. Moreover, unlike convention techniques for diagnosing skin and soft tissue infections, such as blood tests, wound cultures, and other laboratory tests, the diagnostic system 200 can quickly acquire data and produce a classification for the physician to review. The diagnostic system 200 reliably classifies soft tissue conditions, which in turn helps to reduce the misdiagnosis rate, prevent unnecessary hospitalizations, reduce overuse of antibiotics, and save money in healthcare spending. Having generally described the computer system 100 and the diagnostic system 200 in FIGS. 1-2, the present disclosure will now turn to describing methods for using these systems to classify a soft tissue condition in the region of interest of a subject.

Figure 3:
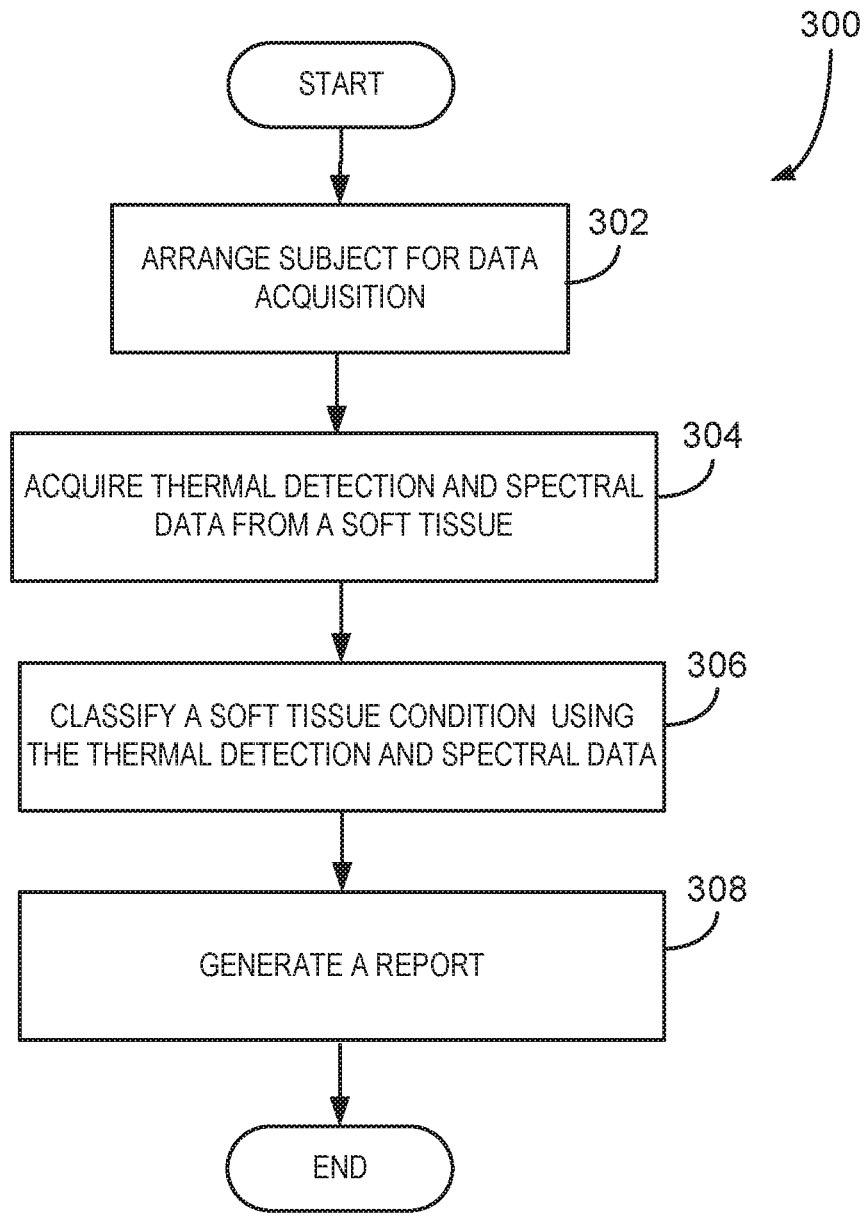
FIG. 3 is a flow chart setting forth the steps of an example method for classifying a soft tissue condition of a subject using thermal image and spectral data in accordance with an aspect of the present disclosure.

Multi-System Model:

Referring to FIG. 3, a flowchart is provided for one implementation of a method 300 for classifying a soft tissue condition using both a thermal detection system and a spectrometer system in accordance with the present disclosure. The method 300 begins at process block 302 by arranging the subject and the diagnostic system 200 in a position for data acquisition. As indicated at 304, thermal detection data and spectral data are then acquired from the soft tissue in the region of interest.

In one aspect, thermal detection data is acquired using the thermal detection system 212. For example, one or more thermal sensor 620 may be configured proximate to the soft tissue to detect infrared radiation. The detected signals may then be processed by the thermal detection system 212 and/or computer system 100 to generate the thermal detection data. The thermal detection data is then used to generate one or more parameter from the thermal detection data.

In one aspect, spectral data is acquired using the spectrometer system 210. For example, the detector 218 may comprise a fiber optic probe that is positioned proximate to an affected region of the subject, and the light source 216 may irradiate the affected area through at least one illumination fiber in the fiber optic probe. The resulting reflected and/or emitted light is then detected using at least one detection fiber in the fiber optic probe of the detector 218. The detected signals are then transferred to the optional spectrometer 214 and/or computer system 100 to generate the spectral data. The computer system 100 then processes the spectral data to generate one or more parameter from the soft tissue in the region of interest As indicated at process block 306, the spectral data and the thermal detection data are then used to classify a soft tissue condition in the region of interest. In one aspect, the at least one processor 104 may classify the soft tissue condition by using a classification model that is built from one or more parameter generated from the input data 102 spectral and thermal detection data. In some aspects, the classification model includes an optimization function that best fits the one or more parameter from the input data to one or more classification option, class label, or attribution set (i.e., classifying the region of interest as cellulitis or pseudocellulitis). That is, the classification model uses the input 102 thermal detection and spectral data to build a model that predicts a classification option of a previously unknown soft tissue condition. The classification model is then applied to the input data to assign or classify the input data to a classification option. As indicated by process block 308, a report may then be generated that includes the classification of the soft tissue condition. The report may be generated and displayed using the computer system 100.

In one non-limiting example, the classification model may identify a soft tissue condition as corresponding to a first classification option (i.e. cellulitis) and a second classification option (i.e., pseudocellulitis), and the classification model may then be applied to the thermal detection and spectral data to identify the soft tissue condition in the region of interest as corresponding to the first classification option or the second classification option.

Suitable input spectral data for the classification model may include one or more parameter from the spectral data, such as a spectral ratio, a blood oxygenation level, and/or a capillary refill time. The blood oxygenation level is typically calculated by the computer system 100 by taking a ratio of the deoxyhemoglobin peak at a spectral absorption of 556 nm and the oxyhemoglobin absorption at a spectral absorption of 549 nm.

Suitable input thermal detection data for the classification model may include one or more parameter from the thermal detection data, such as a temperature difference between an affected area and an unaffected area, or a ratio defined by the temperature difference between the affected area and the unaffected area divided by a temperature in the unaffected area (e.g., a normalized temperature difference). In some aspects the computer system 100 may identify the maximum temperature in the affected area, and use the maximum temperature in the affected area while calculating the temperature differences above. In one non-limiting example, the thermal detection system 212 may be configured to acquire a temperature difference from an external surface of a patient, such as an affected region and an unaffected region. In some aspects, the unaffected region may be located on an unaffected contralateral region or an ipsilateral unaffected region.

The classification model may include a number of classification techniques, such as, but not limited to, decision tree classifiers, rule-based classifiers, neural networks, support vector machines, and linear classification models, such as a linear discriminate analysis (LDA) technique or logistic regression. The soft tissue condition may comprise a skin and soft tissue infection, such as cellulitis or pseudocellulitis.

Figure 4:
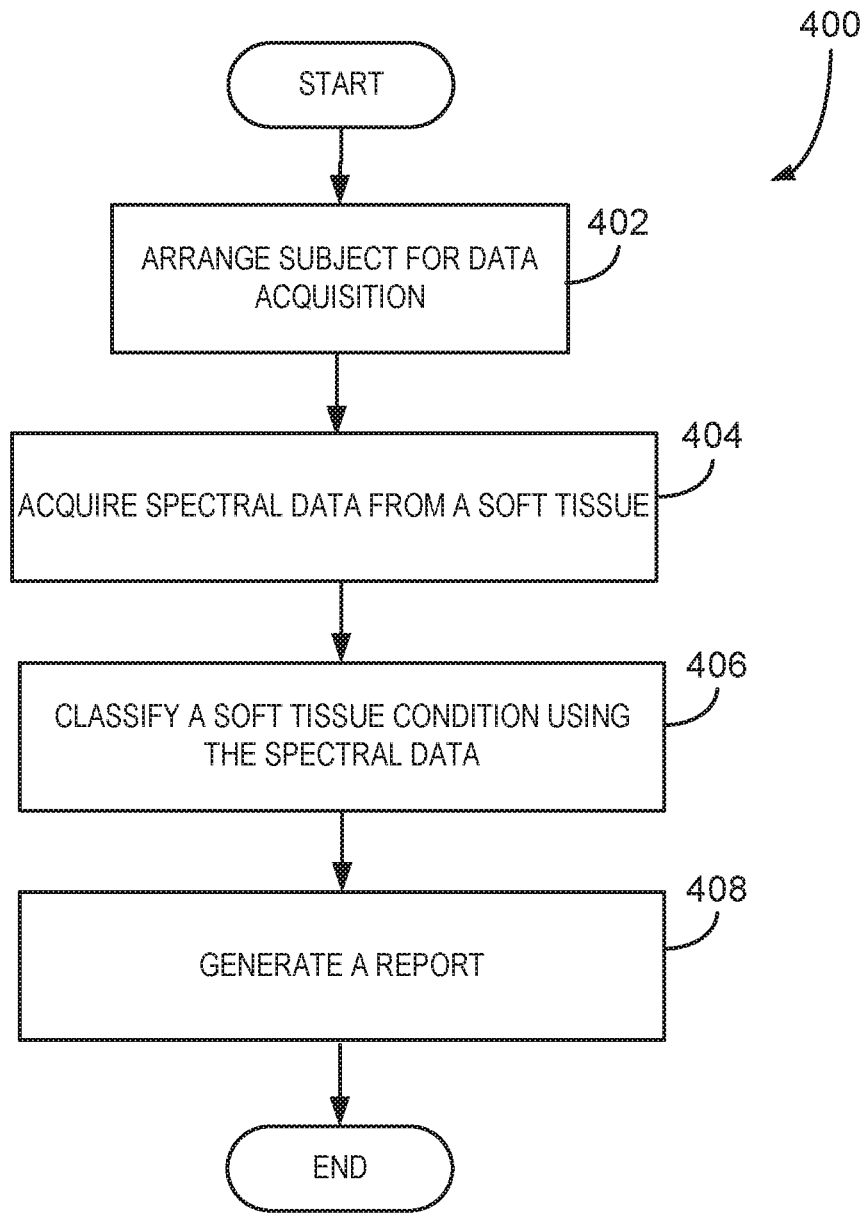
FIG. 4 is a flow chart setting forth the steps of an example method for classifying a soft tissue condition of a subject using spectral data in accordance with another aspect of the present disclosure.

Spectrometer System Model:

Referring to FIG. 4, a flowchart is provided for one implementation of a method 400 for classifying a soft tissue condition using a spectrometer system in accordance with the present disclosure. The method 400 begins at process block 402 by arranging the subject and the diagnostic system 200 in a position for data acquisition. As indicated at 404, spectral data is then acquired from the soft tissue in the region of interest.

In one aspect, spectral data is acquired using the spectrometer system 210. For example, the detector 218 may comprise a fiber optic probe that is positioned proximate to an affected region of the subject, and the light source 216 may irradiate the affected area through at least one illumination fiber in the fiber optic probe. The resulting reflected and/or emitted light is then detected using at least one detection fiber in the fiber optic probe of the detector 218. The detected signals are then transferred to the spectrometer 214 and/or computer system 100 to generate the spectral data. The computer system 100 then processes the spectral data to generate one or more parameter from the soft tissue in the region of interest.

As indicated at process block 406, the spectral data is then used to classify a soft tissue condition in the region of interest. In one aspect, the at least one processor 104 may classify the soft tissue condition by using a classification model. Similar to above, the classification model may be built from input 102 spectral data, for example, by performing an optimization function on one or more parameter from the spectral data to derive a classification threshold or pre-determined value that corresponds to a classification option (i.e., cellulitis or pseudocellulitis). The unknown soft tissue condition is then classified by comparing one or more parameter from the acquired spectral data to the classification threshold.

Suitable spectral data parameters may include, but are not limited to a spectral ratio between a first absorption wavelength and a second absorption wavelength, blood oxygenation level, or capillary refill time. For example, the at least one processor 104 may compute blood oxygenation levels from the spectral data, which may be calculated by taking a spectral ratio between a deoxyhemoglobin peak (~556 nm) and an oxyhemoglobin peak (~549 nm) from the spectral data, the at least one processor 104 may then compare the calculated blood oxygenation level to a pre-determined value. As will be further shown in the examples of the present disclosure, blood oxygenation levels are an effective parameter for classifying soft tissue conditions, such as cellulitis or pseudocellulitis. In one non-limiting example, blood oxygenation levels that exceed 1.012 in the region of interest may be classified as cellulitis, while blood oxygenation levels that are lower than 1.012 in the region of interest may be classified as pseudocellulitis. As indicated by process block 408, a report may then be generated that includes the classification of the soft tissue condition. The report may be generated and displayed using the computer system 100.

Figure 5:
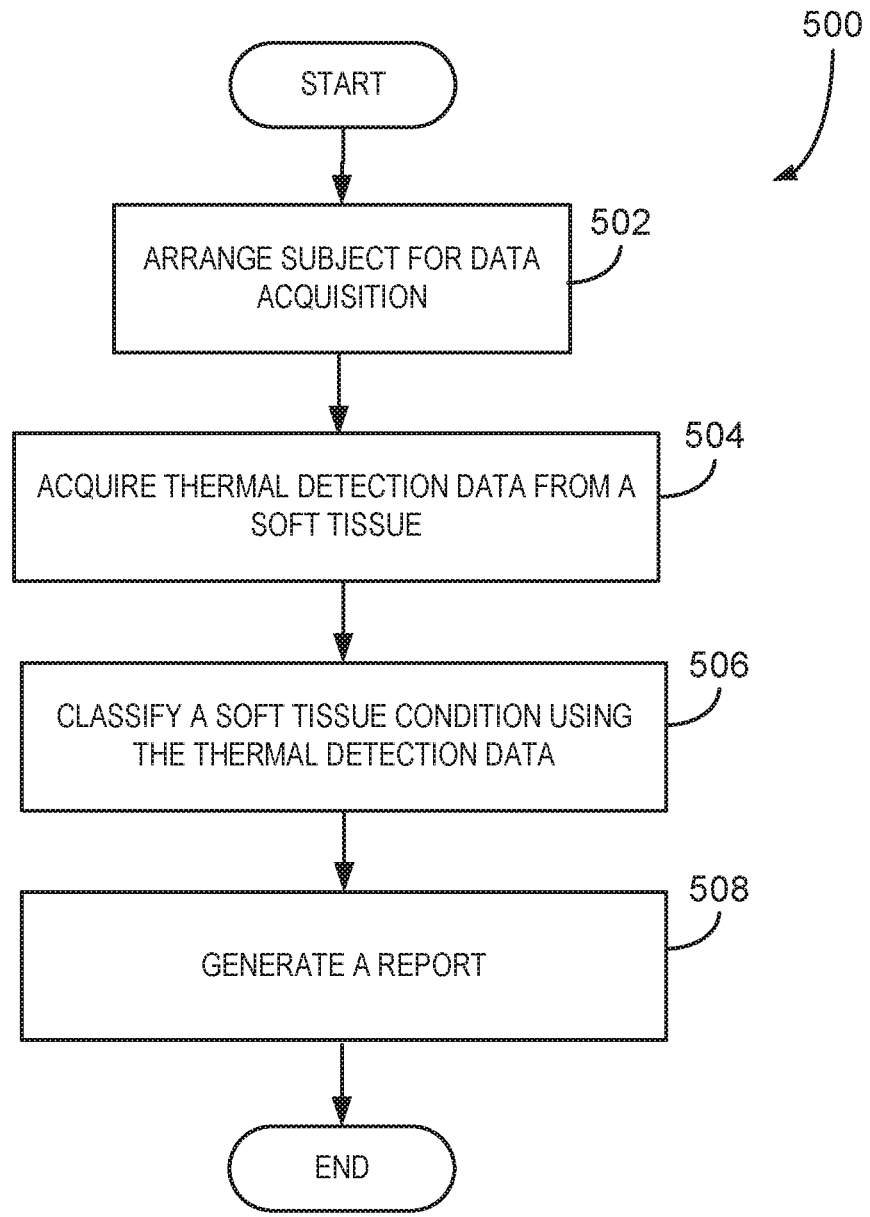
FIG. 5 is a flow chart setting forth the steps of an example method for classifying a soft tissue condition of a subject using thermal detection data in accordance with still another aspect of the present disclosure.

Thermal Detection System Model:

Referring to FIG. 5, a flowchart is provided for one implementation of a method 500 for classifying a soft tissue condition in a region of interest of a subject using a thermal detection system in accordance with the present disclosure. The method 500 begins at process block 502 by arranging the subject and the diagnostic system 200 in a position for data acquisition. As indicated at 304, thermal detection data is then acquired from the soft tissue in the region of interest.

In one aspect, thermal detection data is acquired using the thermal detection system 212. For example, one or more thermal sensor 620 may be configured proximate to the soft tissue to detect infrared radiation. The detected signals may then be processed by the thermal detection system 212 and/or computer system 100 to generate the thermal detection data. The thermal detection data is then used to generate one or more parameter from the thermal detection data.

As indicated at process block 506, the thermal detection data is then used to classify a soft tissue condition in the region of interest. In one aspect, the at least one processor 104 may classify the soft tissue condition by using a classification model. In some aspects, the classification model may be built from the input 102 thermal detection data to derive a classification threshold or a "known" pre-determined value that corresponds to a classification option. The at least one processor 104 then compares one or more parameter from the input 102 thermal detection data to the classification threshold or pre-determined value to classify the soft tissue as corresponding to a classification option (i.e., cellulitis or pseudocellulitis).

Suitable thermal detection parameters may include, but are not limited to a temperature difference between the affected and unaffected area, or a ratio defined by a temperature difference between the affected and unaffected area divided by the unaffected area. As indicated by process block 508, a report may then be generated that includes the classification of the soft tissue condition. The report may be generated and displayed using the computer system 100. In one non-limiting example the soft tissue condition may comprise a skin and soft tissue infection, such as cellulitis or pseudocellulitis.

Figure 6:
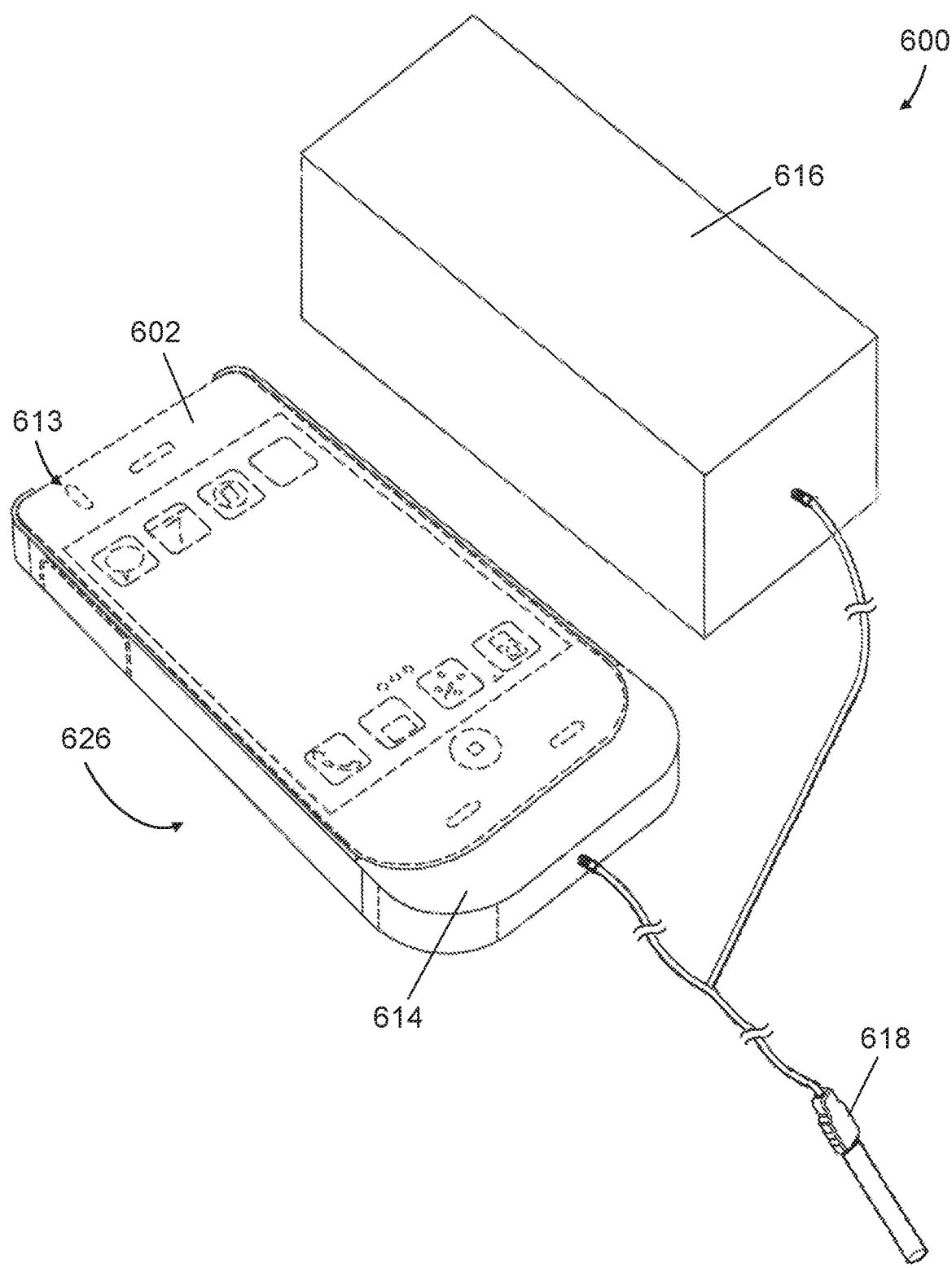
FIG. 6 is a front perspective view of a diagnostic system in accordance with one aspect of the present disclosure.
Figure 7:
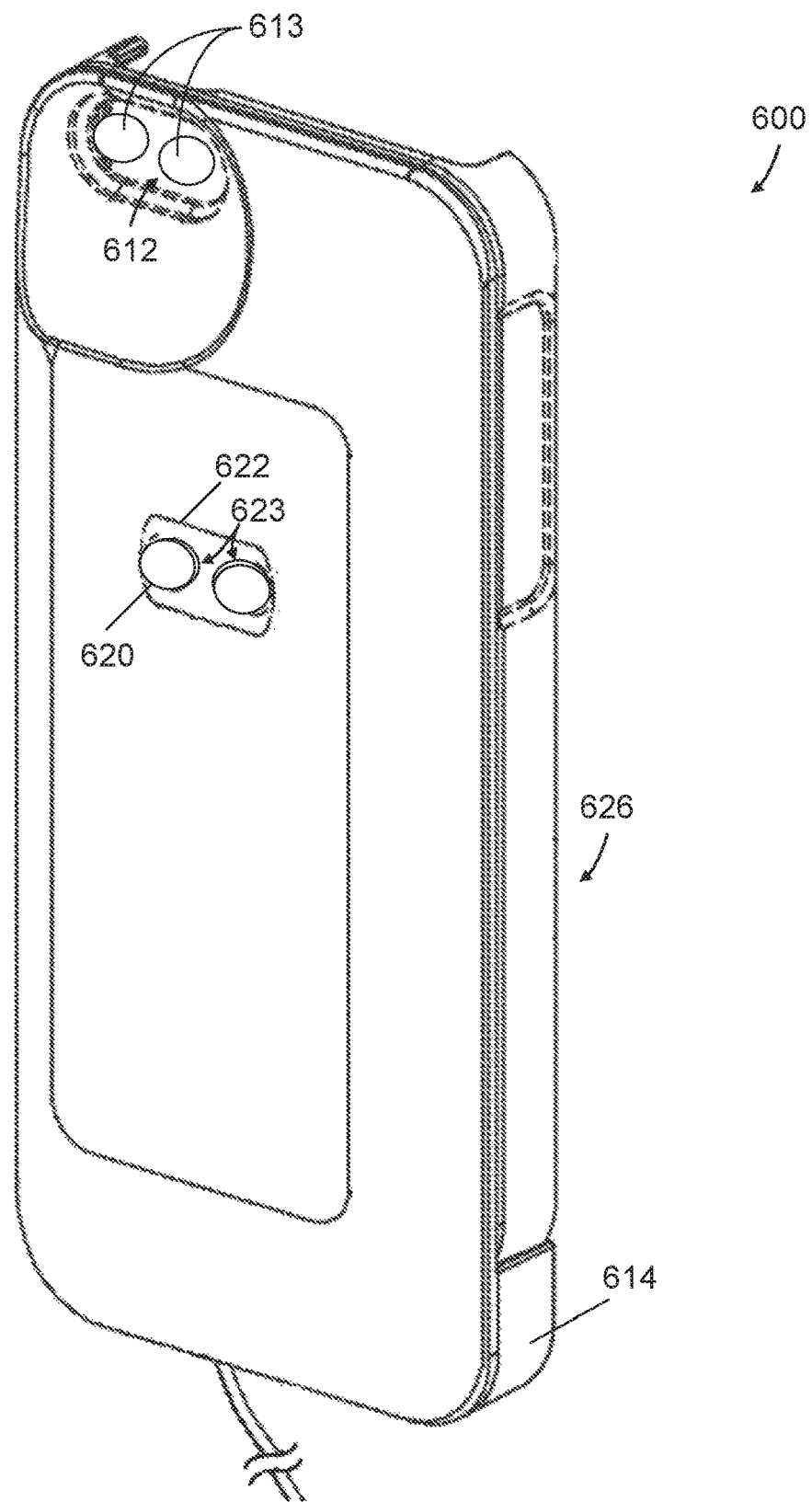
FIG. 7 is a rear perspective view of a diagnostic system of FIG. 6.

Referring particularly now to FIGS. 6-7, an example of a diagnostic system 600 is illustrated that can implement the methods described in the present disclosure. The diagnostic system 600 generally includes a spectrometer 614 and a thermal detection system 612, 620. The spectrometer 614 and the thermal detection system 620 may be configured to form a mobile device attachment 626 that is adapted to receive a mobile device 602. Additionally, or alternatively, the thermal detection system 612 may utilize components, such as lenses 613, that are an integral part of the mobile device 602. In the case of the mobile device attachment 626, the mobile device 602 is communicatively coupled to the spectrometer 614 and the thermal detection system 612 which may take the form of any suitable communicative connection, whether wired, wireless, or a combination of both, such that the mobile device may receive and send information with the spectrometer 614 and the thermal detection system 612. The diagnostic system 600 may further include a detector 618 in the form of a fiber optic probe that is communicatively coupled to the spectrometer 614 and the light source 616. The fiber optic probe may be configured with one or more illumination fiber that is configured to transfer irradiation from the light source 616 to the soft tissue in the region of interest. The fiber optic probe may further include at least one detection fiber that is configured to transfer at least a portion of light that is reflected or emitted from the region of interest to the detector 618 for collection of the spectral data. The collected spectral data may be transferred to the spectrometer 614 and/or to a processor in the mobile device 602 for processing.

In one aspect, the one or more lenses 613 in the mobile device 602 may include a light source, such as white light LED, and camera that may be used to generate the spectral data by irradiating the region of interest at one or more wavelength using the light source in the one or more lenses 613 and acquiring at least a portion of light reflected or emitted from the region of interest using the camera configured within the one or more lenses 613.

In general, the thermal detection system 612 may include one or more thermal sensors 620, an optical element 622 for acquiring imaging data, and/or an actuator 623. In one aspect, the one or more thermal sensor 620 may be configured to acquire thermal detection data by detecting infrared radiation from the soft tissue in the region of interest. The one or more actuator 623 may be used to adjust the focus of the acquired thermal detection data or thermal image data. For example, the one or more actuator may move optical element 622 (i.e., lens), the one or more thermal sensor 620, and other components to focus and defocus the thermal detection data or image, as desired. The mobile device 602 may be used to control the thermal imaging system 612 and the spectrometer system (spectrometer 614, fiber optic probe 618, and light source 616) in the same or similar fashion as described with respect to FIGS. 1-5.

Examples

The following examples set forth, in detail, ways in which the present disclosure may be used or implemented, and will enable one of ordinary skill in the art to more readily understand the principles thereof. The following examples are presented by way of illustration and are not meant to be limiting in any way.

Diffuse Spectroscopy and Thermal Detection Example

Figure 8:
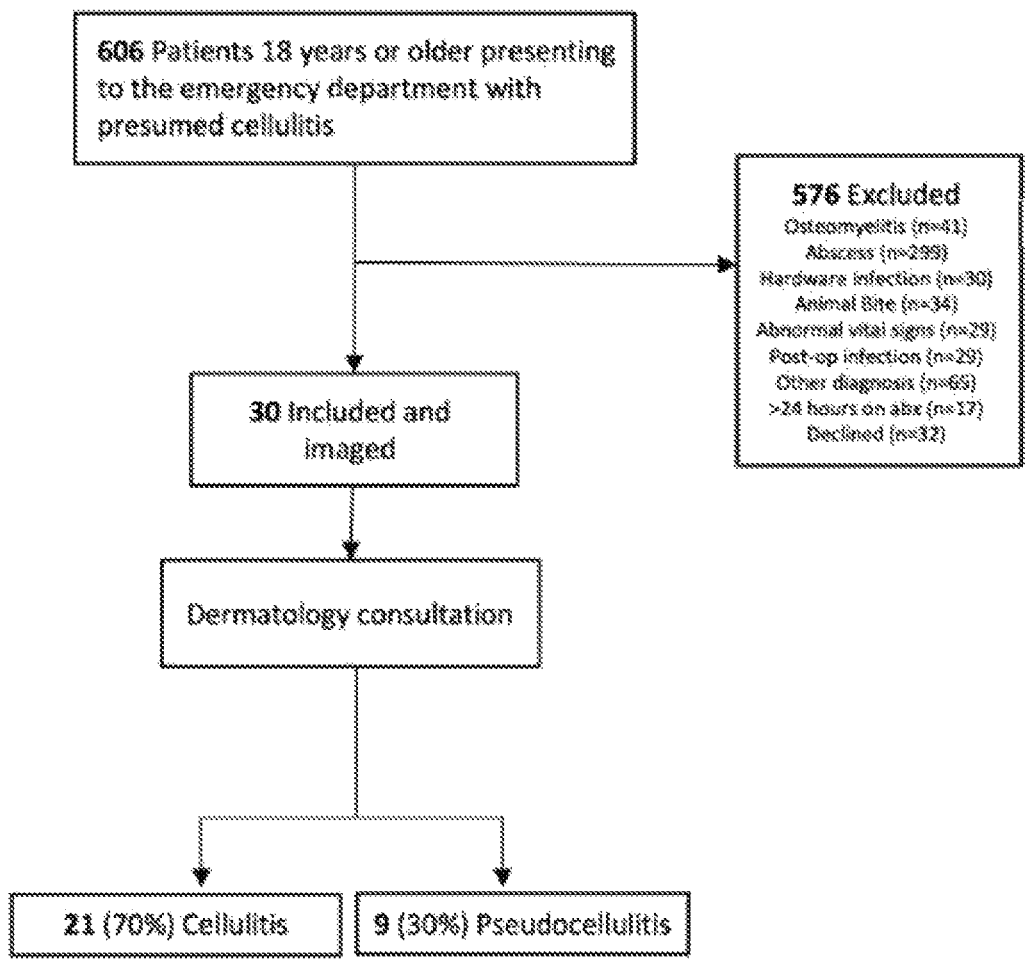
FIG. 8 is a flowchart that shows the screening and enrollment steps for a study in accordance with one aspect of the present disclosure.

A study was conducted to validate the diagnostic system 200, where all patient selection and diagnosis in the study was approved by Partners Institutional Review Board (IRB). Adult patients (≥1.8 years) seen in the Massachusetts General Hospital (MGH) emergency department (ED) with a presumed diagnosis of cellulitis assessed by an ED physician were included after written informed consent was obtained. Patients were excluded if pregnant, a known prisoner, or decisionally impaired. Exclusion criteria included: post-operative site infection (<4 weeks post-operation), hardware/line infection, abnormal vital signs (temperature>100.4° F., pulse>100 bpm), animal/human bite, radiographic evidence of abscess/osteomyelitis, or exposure to intravenous antibiotics for >24 hours. As shown in FIG. 8, 606 consecutive patients were screened for eligibility and 30 patients were enrolled, which left 576 patients excluded. The 30 patients were then given a dermatology consultation where 21 were diagnosed with cellulitis and 9 (30%) were diagnosed with pseudocellulitis. Thermal images and diffuse reflectance spectroscopy (DRS) data were obtained for all 30 enrolled patients. Patient disposition was determined by the ED and medicine teams.

Data were securely managed using REDCap Electronic Data Capture tools. Baseline patient demographics were recorded from direct medical history or chart review, including: age, gender, and race. All patients enrolled had dermatology consultation and final diagnosis of cellulitis or pseudocellulitis was rendered by a board-certified dermatologist. All patients were called or evaluated at a subsequent dermatology office visit within 2 weeks following discharge to assess outcome. If not improved and/or their symptoms suggested an alternate diagnosis, the patient's diagnosis was re-categorized.

The skin spectra were captured with a USB2000 optic fiber spectrometer (Ocean Optics, Dunedin, Fla.), a broadband light source (HL-2000, Ocean Optics, Dunedin, Fla.) and a reflectance fiber probe (QR600-7-SR-125F, Ocean Optics, Dunedin, Fla.). The reflectance probe in contact with the skin consisted of one detection fiber surrounded by 6 illumination fibers, with center to center separation of 0.7 mm and core diameter of 0.6 mm. Integration time was 10 milliseconds. The probe was placed touching the affected skin of the patient without downward pressure. The spectra were normalized to the spectrum of the light source, which was captured using Spectralon reflectance standard (WS-1-SL, Ocean Optics, Dunedin, Fla.) without the probe touching the standard.

The ratio of the spectral intensity at the 556 nm deoxyhemoglobin peak to that of the 542 nm oxyhemoglobin peak ('spectral ratio') was calculated. For a fixed scattering and blood volume, this ratio would tend to be higher for higher blood oxygen saturations. The mean spectral ratios were compared using a two-sided student t-test at a significance level of 0.05. To determine the best spectral ratio threshold for classification, a logistic regression was calculated using R statistical software (version 3.2.2). The logistic regression returns a sigmoid model which assigns to each ratio a probability of cellulitis. The ROC curve and AUC were subsequently generated.

Figure 9:
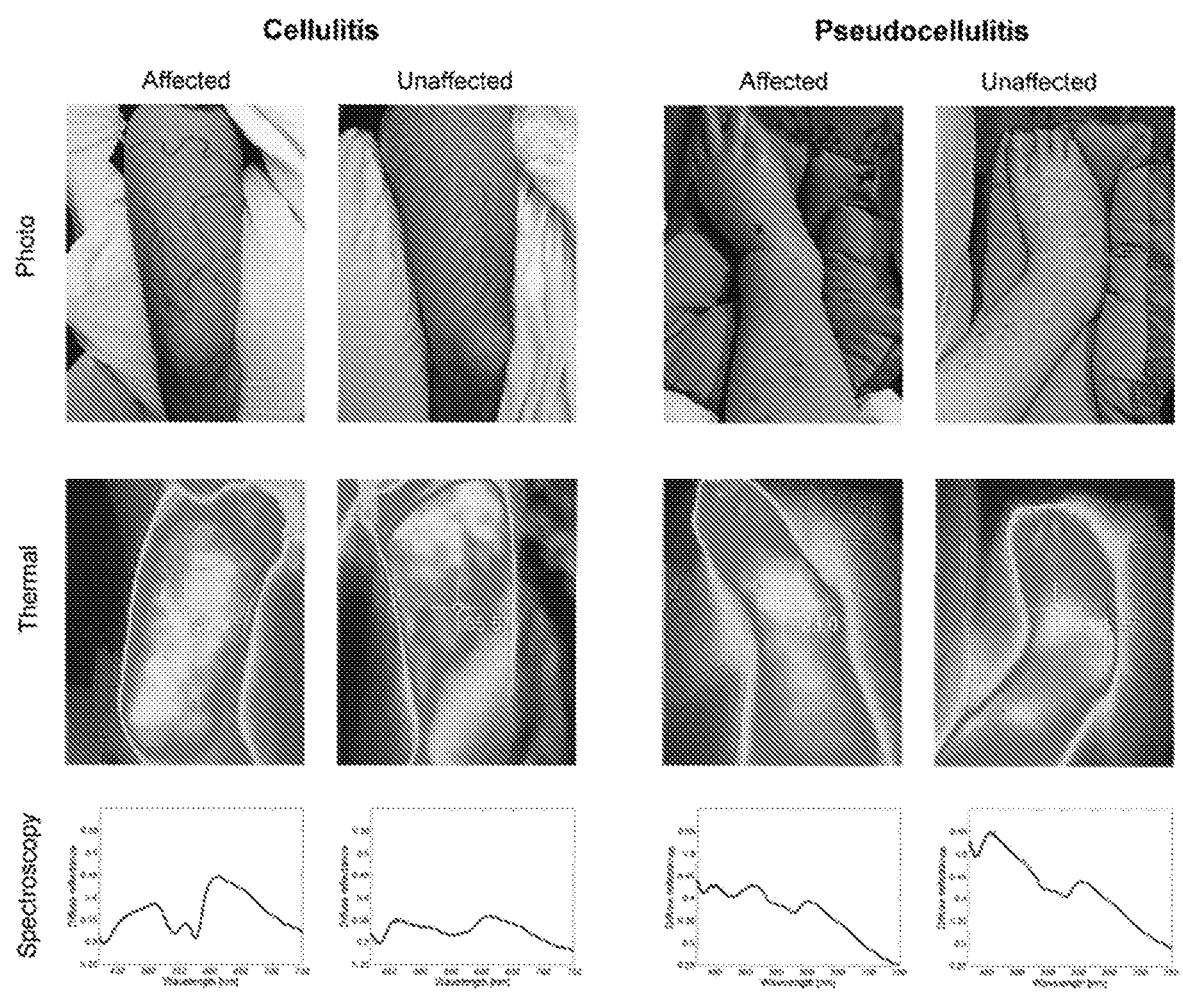
FIG. 9 is a series of clinical images, thermal images, and diffuse reflectance spectroscopy spectra of representative patients. Representative data for the affected and unaffected areas of skin. For cellulitis patient, the temperature difference (affected−unaffected) was 1.4° C. For the pseudocellulitis patient, the temperature difference was −3.6° C.

Skin temperature was measured at the point of maximal temperature on the affected body part as determined by localizing the warmest area on the live thermal image. Unaffected skin surface temperature of the exact corresponding region of the contralateral body part was measured (FIG. 9). In cases where affected skin was present bilaterally, unaffected skin surface temperature of the ipsilateral proximal extremity was imaged. All temperature measurements were taken within 24 hours of ED presentation. Measurements were taken with a thermal imaging camera, which takes thermal images with temperature measurements between −20° C. and 120° C. without contacting the object. This smartphone attachment detects temperature differences as small as 0.1° C. The camera was held approximately 30 centimeters from the skin. The consulting dermatologist was blinded to the thermal images, and had no access to the photos until reviewing them for quality. During quality control, images were coded and reviewers blinded to final diagnosis. The temperature difference (affected minus unaffected) were calculated.

Figure 10:
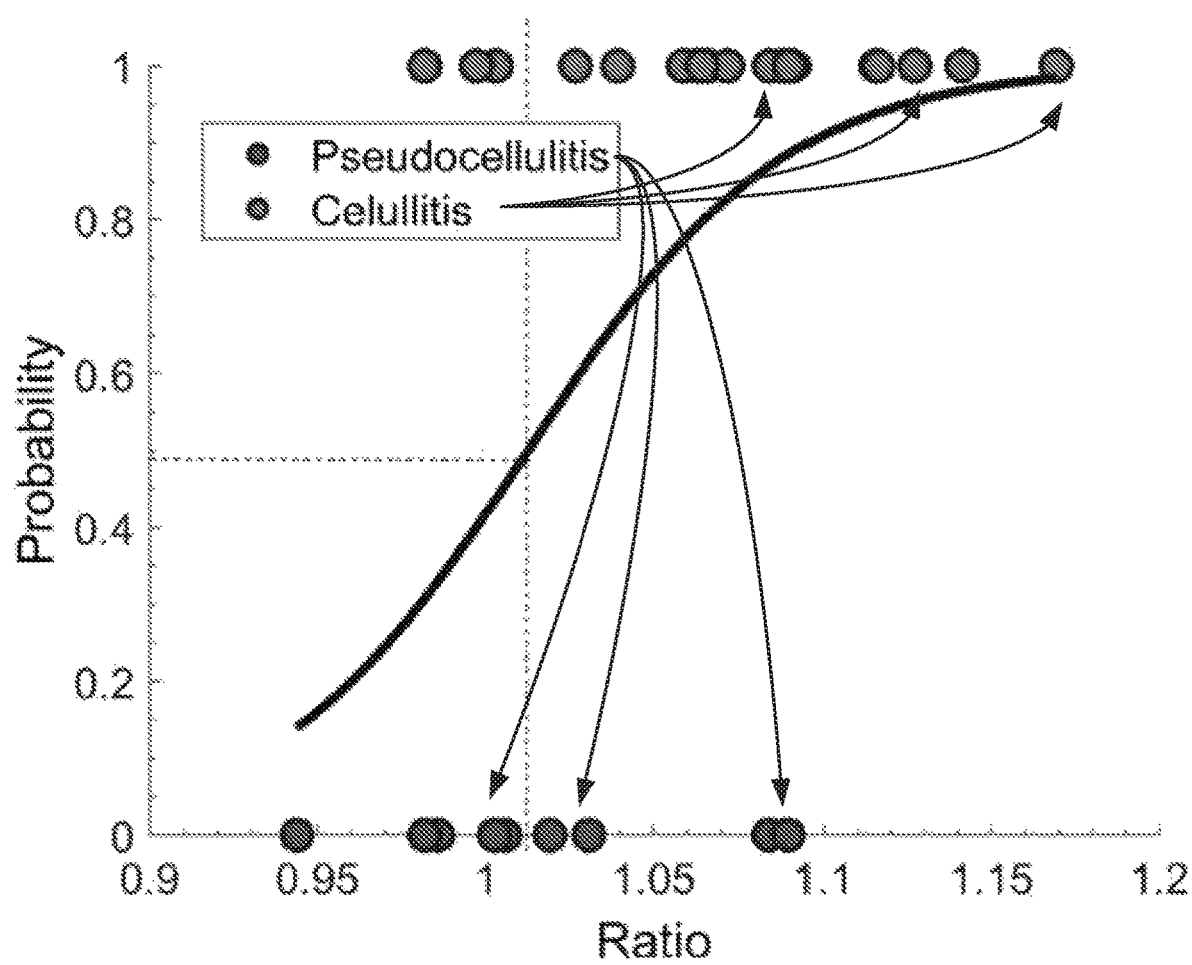
FIG. 10 is a classification model in accordance with one aspect of the present disclosure. The classification model includes a logistic regression that determined the probability of cellulitis based on a spectral ratio (556/542 nm) of the affected skin. 50% threshold corresponds to a spectral ratio of 1.012.

A linear classifier was calculated for the thermal differences and the spectral ratios using a linear discriminate analysis (LDA) technique. This technique returns the slope and the intercept of the line that best separates the two groups (cellulitis and pseudocellulitis) in the thermal difference and spectral ratio scatter plot (FIG. 10). By changing the intercept of the line, optimal sensitivity and specificity of the classifier can be selected. A receiver operating characteristic (ROC) curve and area under the curve (AU C) of this model was generated. We used cross-validation (stratified 'leave-p-out' technique, p=6) to predict the model's future generalizability. In this approach, 6 observations (validation set) are randomly removed from the dataset and the remaining 24 (training set) are used to build the LDA classifier. Once the classifier is calculated, it is used to predict the class membership of the observations on the validation set. The prediction is compared to the actual diagnosis. This is repeated for a different random validation set. Only validation sets in which the ratio of cellulitis to pseudocellulitis observations is the same as in the population (4:2, given 70% of the cases are expected to be cellulitis) are kept. The process is repeated until all possible validation sets are exhausted (total of 215,460 different sets). Finally, the average classification performance is calculated.

Results: all patients were seen in dermatology consultation and a diagnosis of cellulitis or pseudocellulitis was rendered by the dermatologist. Of 30 patients, 21/30 (70%) were diagnosed with cellulitis and 9/30 (30%) were diagnosed with pseudocellulitis (FIG. 8). This misdiagnosis rate is consistent with prior studies. Given dermatologists have been suggested as the 'gold standard' for cellulitis diagnosis, these dermatology-validated diagnoses were used to build the predictive models. The median patient age was 53.6 years old (IQR 38.8-67.3). The study group was comprised of 18 men (60%) and 12 women (40%). There was a statistically significant difference in age but not race between patients with cellulitis compared to those with pseudocellulitis, as shown in Table 1.

TABLE 1

Baseline patient demographics for patient with cellulitis and pseudocellulitis; IQR: interquartile range.

|  | Total (n = 30) | Cellulitis (n = 21) | Pseudocellulitis (n = 9) | p-value |
|---|---|---|---|---|
| Age, mean (IQR) | 53.56 (38.84-67.28) | 48.1 (32.9-58.47) | 66.29 (64.75-76.25.6) | 0.013 |
| Gender, n (%) |  |  |  | 0.051 |
| Male | 18 (60%) | 15 (71%) | 3 (33%) |  |
| Female | 12 (40%) | 6 (29%) | 6 (67%) |  |
| Race, n (%) |  |  |  | 0.59 |
| White | 25 (84%) | 17 (81%) | 8 (89%) |  |
| Asian or Pacific Islander | 1 (3%) | 1 (5%) | 0 (0%) |  |
| American Indian | 0 (0%) | 0 (0%) | 0 (0%) |  |
| Black | 1 (3%) | 1 (5%) | 0 (0%) |  |
| Hispanic | 3 (10%) | 2 (9%) | 1 (11%) |  |

Spectra of the affected skin area were assessed by ratiometric analysis of the spectral intensity at the 556 nm deoxyhemoglobin peak to that of the 542 nm oxyhemoglobin peak ('spectral ratio'). Given a fixed scattering and blood volume, a higher ratio suggests higher blood oxygen saturations. In cellulitis, the mean of the spectral ratios was significantly higher compared to patients with pseudocellulitis (1.0736 [95% CI 1.0536-1.0936] vs 1.0159 [95% CI 0.9849-1.0469], p=0.0048, Table 2). Table 2 shows spectral ratios for patients with cellulitis and pseudocellulitis. Specifically, Table 2 shows a mean of the spectral ratio between 556 nm (deoxyhemoglobin peak) to 542 (oxyhemoglobin peak) that was calculated for the affected skin in patients with cellulitis and pseudocellulitis. The mean spectral ratios were compares using a two-sided student t-test at a significance level of 0.05. This suggests the spectral ratio is a useful metric in discriminating cellulitis from pseudocellulitis.

TABLE 2

Cross-validation of the Dual Parameter Model.

| Ratio 556/542 nm | Cellulitis | Pseudocellulitis |
|---|---|---|
| Mean | 1.0736 | 1.0159 |
| SD | 0.0472 | 0.0473 |
| N | 21 | 9 |

A classification threshold was determined using logistic regression for predicting cellulitis based on the spectral ratio alone (FIG. 10). According to this model, a spectral ratio of ≥1.012 corresponded to a 50% probability of cellulitis and, using this threshold, the spectral ratio model alone has a classification sensitivity of 86%, specificity of 56%, positive predictive value (PPV) of 82%, negative predictive value (NPV) of 63%, and accuracy of 77%. For comparison, the standard of care clinical diagnosis (classifying all patients as cellulitis with an expected 30% misdiagnosis rate) has an accuracy of 70%. While this spectral ratio model alone demonstrates an improvement over standard of care, we assessed whether a dual parameter predictive model using both the skin temperature and spectral ratio could provide higher accuracy.

Figure 11:
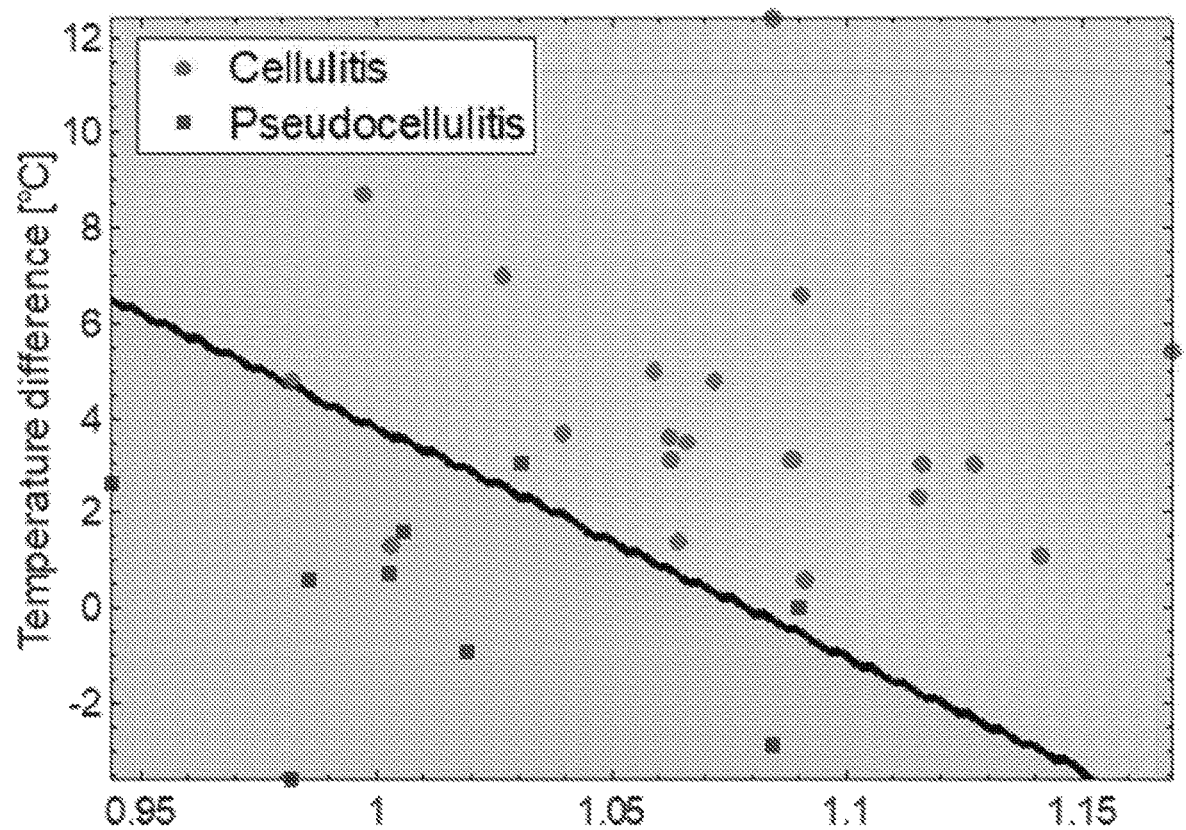
FIG. 11 is classification model built from one or more parameter from spectral and thermal detection data. The classification model includes a linear classifier that was calculated for the thermal differences and the spectral ratios using a linear discriminant analysis technique. By changing the intercept of the line, optimal sensitivity and specificity of the classifier can be selected. We demonstrate a sensitivity of 95.2%, specificity of 77.8%, PPV of 90.9%, NPV of 87.5%, and accuracy of 90.0%
Figure 12:
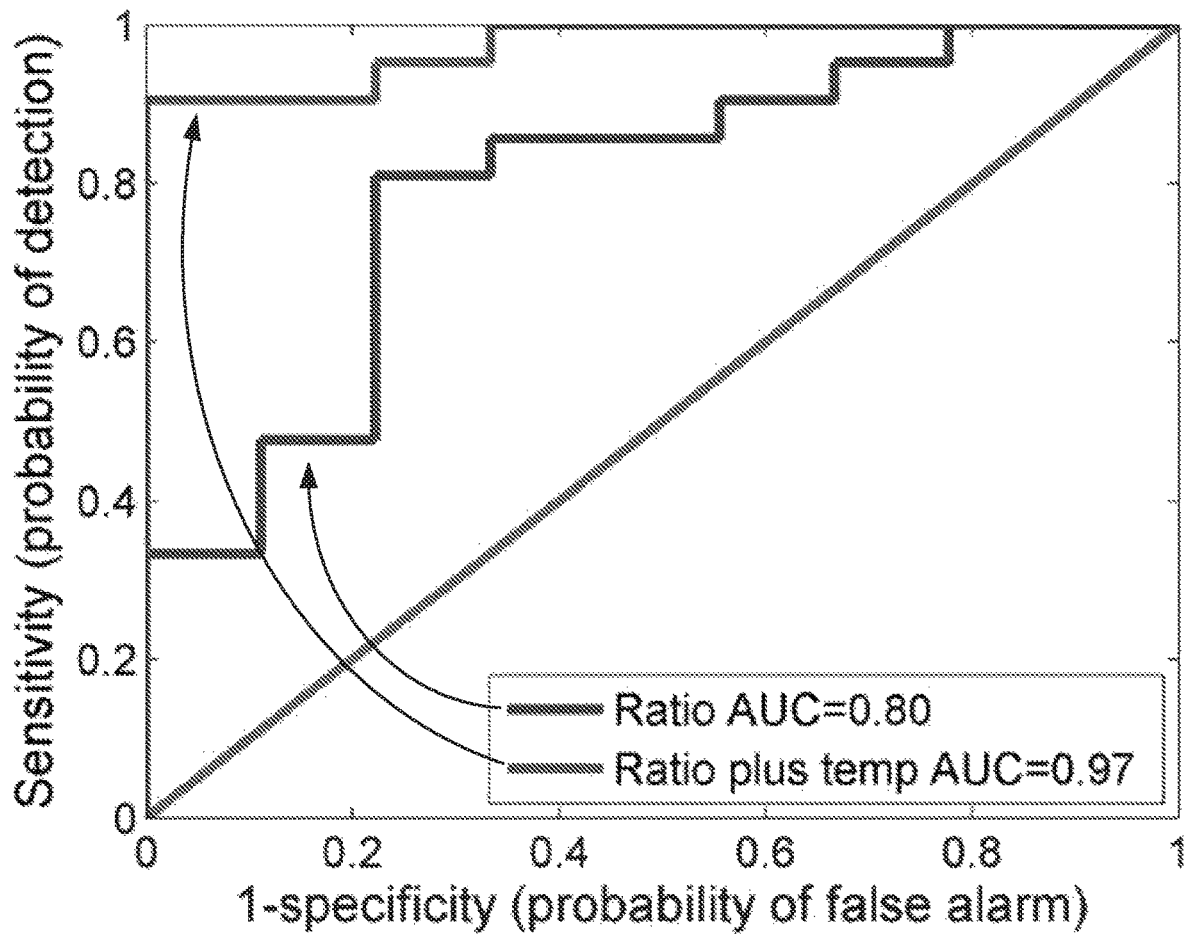
FIG. 12 is a Receiver operating characteristic (ROC) curve. ROC curve for predicting cellulitis in using spectral ratio predictive model alone and dual parameter predictive model.

Measuring the skin temperature difference between affected and unaffected skin can differentiate cellulitis from pseudocellulitis with an accuracy of approximately 82.5%. Combining this skin temperature difference with the spectral ratio in a scatter plot, it is observed that the cellulitis cases cluster towards the upper right quadrant, while pseudocellulitis cases cluster towards the lower left quadrant (FIG. 11). Using linear discriminant analysis (LDA) to create a new classifier, a higher accuracy was demonstrated compared to using either the temperature difference or spectral ratio predictive models alone, with sensitivity of 95.2%, specificity of 77.8%, PPV of 90.9%, NPV of 87.5%, and accuracy of 90.0%. The receiver operating characteristic (ROC) curve for both the spectral ratio alone and the dual parameter model are shown in FIG. 12, where the AUC for the dual parameter model is 0.97.

To validate the dual parameter model in the absence of a separate validation set, a 'leave-p-out' cross-validation was performed. The average result of the cross-validation predicts an accuracy classification of 86.8% for future samples (Table 3). Table 3 shows a stratified 'leave-p-out' technique (p=6) used to predict the model's future generalizability. A total of 215,460 different sets were used. The average classification performance is presented as a mean and standard deviation (SD).

TABLE 3

Cross-validation of the dual parameter model.

| Statistic | Mean | SD |
|---|---|---|
| Accuracy | 0.8681 | 0.1280 |
| Sensitivity | 0.9138 | 0.1347 |
| Specificity | 0.7766 | 0.2790 |
| Positive predictive value | 0.9054 | 0.1166 |
| Negative predictive value* | 0.8611 | 0.2181 |

Using a combined model of skin temperature and DRS differentiates cellulitis from pseudocellulitis with an accuracy of 90%. Using our defined ratiometric threshold, a ratio higher than ≥1.012 from the affected area of skin suggests a diagnosis of cellulitis. While this classifier alone demonstrates improved accuracy compared to clinical diagnosis, there is significant improvement when the additional classifier of temperature difference. A higher temperature difference suggests a diagnosis of cellulitis. The combined dual parameter model has a very high AUC (0.97)—more than both the spectral ratio (0.80) and temperature difference (0.86) alone—indicating a greater utility in predicting cellulitis.

Cellulitis is primarily managed by primary care, ED, or internal medicine. While dermatology or infectious disease consultation improves diagnostic accuracy, the potential demand far outweighs supply. Given no objective diagnostic tools exist for cellulitis, this dual parameter classification technique could improve diagnostic accuracy in the absence of dermatology consultation.

In order to validate the results given the sample size, a cross-validation with a 'leave-p-out' technique was used. This technique uses the 'p' observations as the validation set and the remaining observations as the training set. This is repeated until all possible validation sets are exhausted. The main assumption for this technique is that the observations in our dataset are representative of the overall population. In this study, the misdiagnosis rate (30%) aligns with findings in previous studies, suggesting it is representative. With the 'leave-p-out' technique, when the 'p' is large, the cross-validation tends to be overly pessimistic, therefore we selected p=6 (20%) as a compromise with a reasonable number of possible combinations (total of 215,460 different sets). The predicted PPV (90.5%) and accuracy (86.8%) of our cross-validation (Table 3) predicts the performance for future samples in the general population, and demonstrate improved performance compared to standard of care.

One possible advantage of using thermal imaging alone to diagnose cellulitis is that it is not impacted by skin melanin content, which can obscure the visual perception of underlying erythema in darker skin types. While DRS identifies absorption characteristics of multiple skin parameters—including melanin, water, lipids, and others—ratiometric method presented herein highlights data from the deoxygenated and oxygenated hemoglobin peaks, canceling out contributions from other skin components which do not significantly contribute to absorption at the specified wavelengths (556/542 nm). In addition, the scattering component is compensated by choosing two wavelengths close together. As a result, DRS findings are broadly generalizable to patients of all skin types and may be more accurate than clinical observation alone.

It is also contemplated that a near-infrared ratiometric approach may be used as well. The near-infrared ratiometric approach probes deeper into the dermis compared to the green wavelengths used. Further, more sophisticated measurements such as diffuse optical spectroscopy are contemplated in the present disclosure as well. The data presented herein strongly suggests that the simple two-wavelength measurement of diffuse reflectance is sufficient; however using multiple wavelengths (i.e., greater than two) could be used in the classification model as well. Implementation of our dual parameter technique to diagnose cellulitis can be easy and inexpensive. While this study utilized sophisticated equipment for both the temperature and spectral measurements, simpler instruments could be used.

The results of the current study demonstrate that spectral ratios from DRS combined with skin temperature can accurately differentiate soft tissue conditions, such as classifying cellulitis from pseudocellulitis. Spectroscopy and thermal imaging are easy to use, low-cost, and non-invasive, and this dual parameter model may reduce cellulitis misdiagnosis, unnecessary hospitalization, antibiotic overuse, and healthcare costs.

Thermal Imaging System Example

Figure 13:
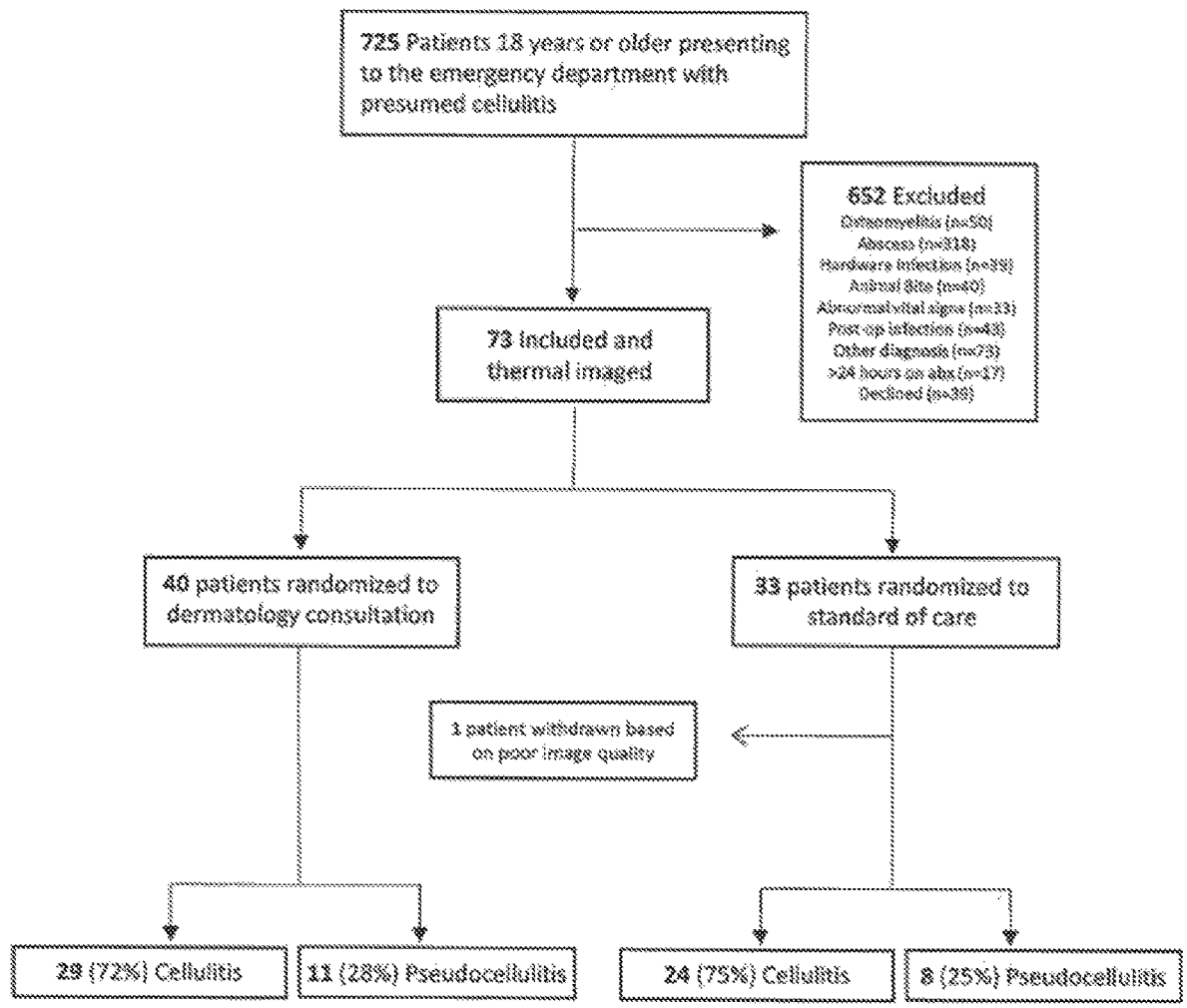
FIG. 13 is a flowchart that shows the screening and enrollment steps for a study in accordance with an aspect of the present disclosure.

A study was conducted with adult patients (>18 years old) seen in the Massachusetts General Hospital (MGH) Emergency Department (ED) in Boston, Mass. with a presumed diagnosis of cellulitis were included in this study. Patients were excluded if they were pregnant, a known prisoner, or decisionally impaired. As shown in FIG. 13, approximately 725 patients were screened for eligibility and 73 patients were enrolled, leaving 652 excluded from the study. The study screening shown in FIG. 13 was part of a larger randomized control study, the goal of which was to determine the role of dermatologic consultation on outcomes of patients with presumed diagnosis of cellulitis. Seventy-three patients were randomized in a 1:1 ratio using a random number generator, 40 of whom were seen by dermatology consultation and 33 of whom were randomized to standard of care (management by ED and medicine teams). One patient from the standard of care cohort was withdrawn from further analysis due to poor image quality. Of the patients seen by a dermatology consultation, 29 (72%) were diagnosed with cellulitis and 11 (28%) were diagnosed with pseudocellulitis. Of the patients seen by the standard of care (management by ED and medicine teams), 24 were diagnosed with cellulitis and 8 were diagnosed with pseudocellulitis. Partners Healthcare Institutional Review Board approval was obtained for this study.

In addition, patients with any of the following were excluded: post-operative site infection (less than 4 weeks post-operation), hardware or line infection, abnormal vital signs (body temperature>100.4° C., pulse>100), animal or human bite, or radiographic evidence of abscess or osteomyelitis.

Baseline patient demographics were recorded for every patient who enrolled, either from direct medical history or from chart review. These included: age, gender, past medical and surgical history, and assessment of cellulitis risk factors (i.e. chronic lymphedema, tinea pedis, onychomycosis, type II diabetes, history of trauma, end stage renal disease, active cancer, HIV/AIDs, neutropenia, and immunosuppressive medications). The final discharge diagnosis for each patient was also recorded. In the cohort randomized to dermatology consultation, diagnosis was made by a board-certified dermatologist. In the cohort managed by standard of care, patients who were discharged with a diagnosis of cellulitis were categorized as having cellulitis, while those who were given an alternative diagnosis during hospitalization, discharge, or within 30 days of discharge were considered to have pseudocellulitis.

Figure 14:
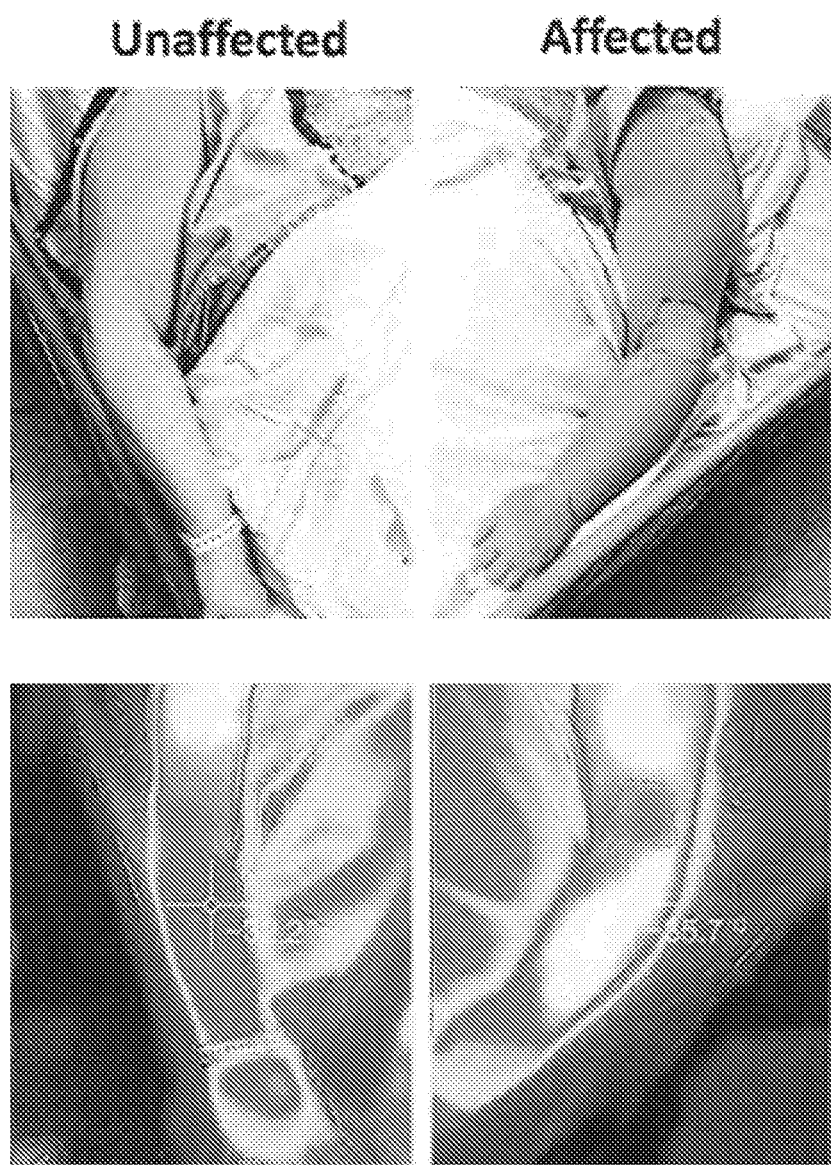
FIG. 14 is a pair of clinical images and corresponding thermal images for an unaffected and affected skin area of a representative in the study that is diagnosed with cellulitis. Temperature difference of the affected minus the unaffected area was 3.5° C.
Figure 15:
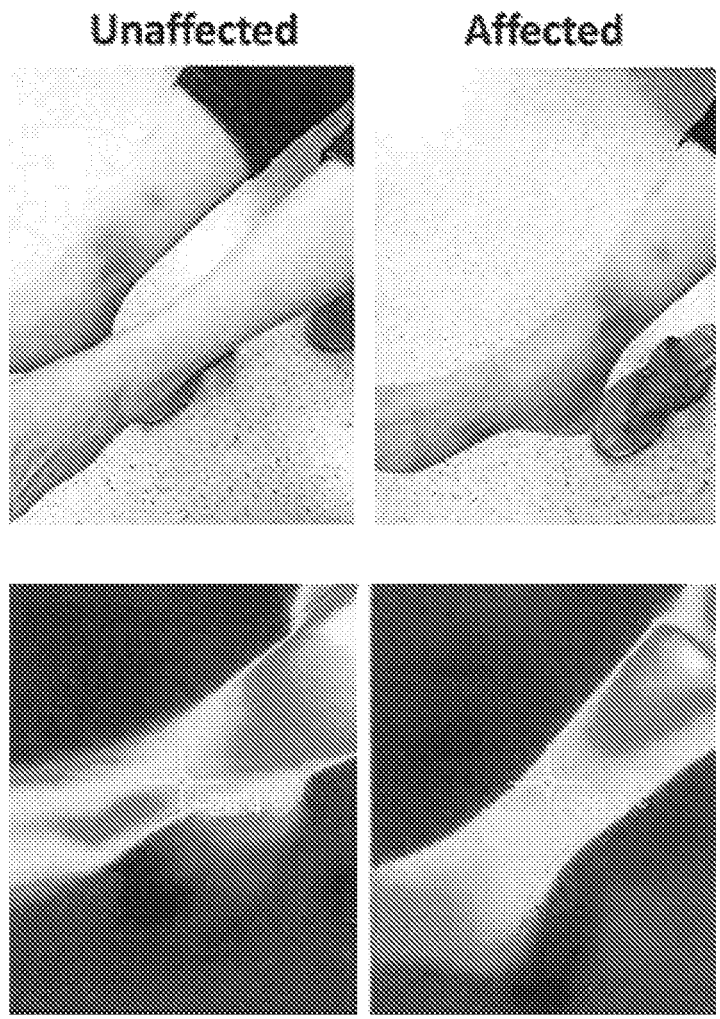
FIG. 15 is pair of clinical images and corresponding thermal images of an unaffected and affected area of skin of a representative in the study that is diagnosed with pseudocellulitis. Temperature difference of affected–unaffected is 0.1° C.

Skin surface temperature was measured at the point of maximal temperature on the affected body part as determined by localizing the warmest area on the live thermal image. Subsequently, unaffected skin surface temperature of the exact corresponding region of the contralateral body part was measured (FIG. 14 and FIG. 15). In cases where affected skin was present bilaterally, unaffected skin surface temperature of the ipsilateral proximal extremity was imaged. All temperature measurements were taken within 24 hours of ED presentation. Measurements were taken with a thermal camera that enables thermal images and temperature measurements to be taken between −20° C. and 120° C. without contacting the object. This light-weight device attaches to a smartphone and can detect temperature differences as small as 0.1° C. The camera was held approximately 30 centimeters from the skin surface. For each patient, the same health care worker took both photos, one on the affected skin area and the other unaffected skin area.

The physician who made the final diagnosis for each patient was blinded to the thermal imaging measurements in the study and had no access to the photos until reviewing them for quality control. During quality control, photos were coded and reviewers were blinded to final diagnosis. For three patients, in which the temperature was not recorded on the thermal image directly, an application tool in the thermal imaging camera was employed to assess the image's temperature reading. In addition, the application tool was used to find the maximal temperature per anatomic subunit for all images of the affected skin to validate the localization of the warmest spot on the live thermal image as determined by the imagers.

All study data were securely collected and managed using REDCap Electronic Data Capture tools hosted at Massachusetts General Hospital and analyzed using SAS 9.4 (SAS, Cary, N.C.). Average skin temperatures in the affected and unaffected areas were obtained for those with final diagnosis of cellulitis and those with pseudocellulitis. The difference in these averages was calculated within each group of patients as well as between the two groups. 95% confidence intervals were obtained using the percentile method for these differences based on 10,000 bootstrap samples. A two-sided t-test was used to test for the statistical significance of the group difference at a significance level of 0.05.

Figure 16:
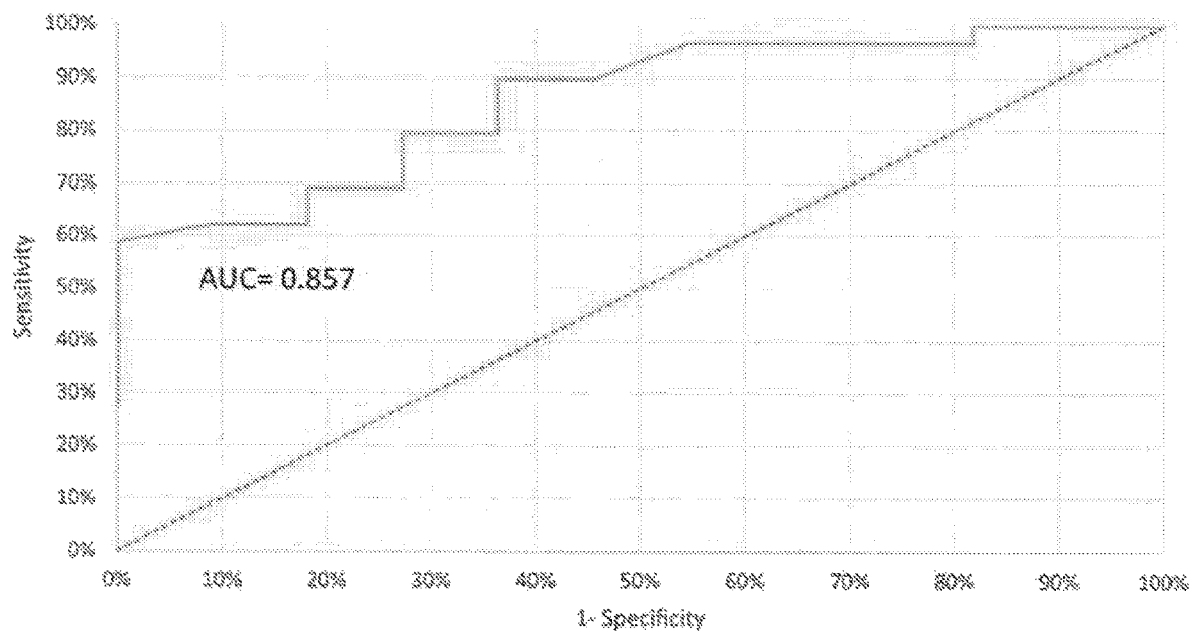
FIG. 16 is a graph showing receiver operating characteristic (ROC) curve. ROC curve for predicting cellulitis in patients randomized to dermatology consultation (n=40).
Figure 17:
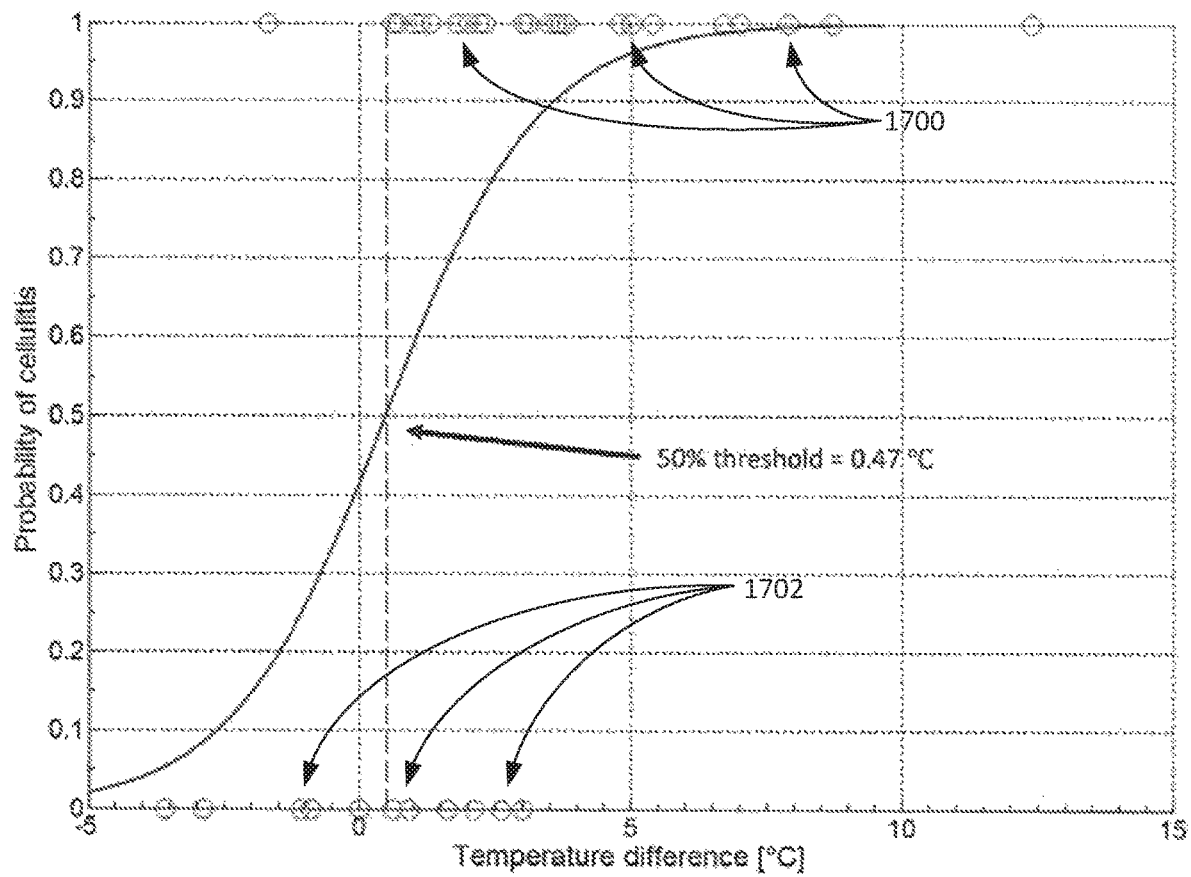
FIG. 17 is a graph showing a classification model in accordance with an aspect of the present disclosure. The classification model includes a logistic regression that shows the probability of cellulitis based on temperature difference between affected and unaffected skin. 50% threshold corresponds to 0.47° C.
Figure 18:
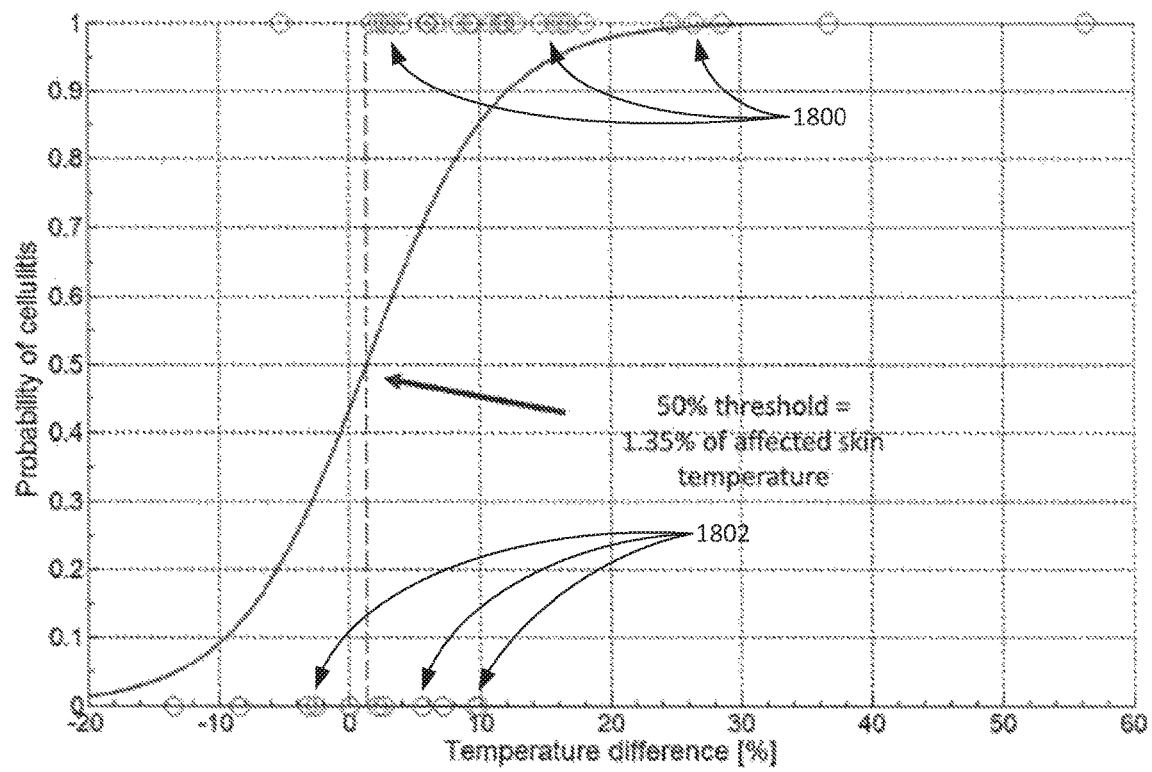
FIG. 18 is a graph showing a classification model in accordance with an aspect of the present disclosure. The classification model includes a logistic regression that shows probability of cellulitis for a ratio defined by a given temperature difference divided by an unaffected skin temperature. 50% threshold exists at 1.35%.

The receiver operating characteristic (ROC) curve and area under the curve (AUC) were obtained based on the patients in the dermatology consultation cohort (n=40) (FIG. 16). Subsequently, logistic regression was employed on the imaging data of this group to develop predictive models, as prior studies have shown that dermatology consultation has high diagnostic accuracy for cellulitis. Two models were created via logistic regression; the first (Model 1) quantifies the probability of cellulitis diagnosis 1700 or the identification of pseudocellulitis 1702 based on the temperature gradient between affected and unaffected skin, as shown in FIG. 17. Model 2 determined probability of cellulitis diagnosis 1800 or the identification of pseudocellulitis 1802 based on the temperature gradient as a percentage of the unaffected skin temperature (FIG. 18). Subsequently, the two models were analyzed for the ability to accurately predict the ultimate diagnosis of the cohort managed by standard of care (n=32).

Of 72 enrolled and included patients (FIG. 13), the median patient age was 58.7 years old (interquartile range: 44.5-73.9). The study group was comprised of 43 men (59.7%) and 29 women (40.3%) (FIG. 19). There were no significant differences in baseline demographics between the two randomized groups (FIG. 20). There were no significant differences in risk factors between patients diagnosed with cellulitis compared to those diagnosed with pseudocellulitis (FIG. 19). The most common site of cellulitis infection was the lower extremity (81%), with 10% affecting the upper extremity, 6% the head and neck, and 3% the trunk.

Among study participants, 40 were randomized to dermatologic consultation and 32 were randomized to standard of care (management by ED or medicine team). Within the cohort randomized to dermatology consultation, 29/40 patients (72%) were diagnosed with cellulitis, while 11/40 patients (28%) were diagnosed with pseudocellulitis. Of the patients randomized to standard of care, 24/32 (75%) patients were discharged with a diagnosis of cellulitis, while 8/32 (25%) patients were discharged with a diagnosis of pseudocellulitis. Alternative diagnoses in both groups can be found in FIG. 21. There were no adverse events in either group.

Skin temperatures were analyzed of the 40 patients randomized to dermatology consultation. In patients with cellulitis, the average temperature of the affected area was 34.1° C., and the unaffected area was 30.4° C., yielding a difference of 3.7° C. (95% CI 2.7-4.8° C., p=0.00001). In patients diagnosed with pseudocellulitis, the average temperature of the affected area was 31.5° C. and the unaffected area was 31.3° C., yielding a difference of 0.2° C. (95% CI-1.1-1.5° C., p=0.44) (FIG. 22). Difference in the affected skin temperature between patients with cellulitis and pseudocellulitis was statistically significant (2.6° C., 95% CI: 0.7-4.6 p=0.008), as was the temperature difference in temperature gradients (3.5 C, 95% CI: 1.9-5.2, p=0.002) (FIG. 22).

Receiver operating characteristic (ROC) curve and area under the curve (AUC) were calculated based on temperature differences between affected and unaffected skin for patients in the dermatology consultation cohort (n=40) (FIG. 16). The AUC was 0.857. Logistic regression was employed to create classification models for predicting cellulitis based on skin surface temperature measurements of this cohort (FIG. 17). We chose to present a classification model which predicted cellulitis diagnosis from temperature difference between affected and unaffected skin, and found that a temperature difference of 0.47° C. corresponded to a 50% probability of cellulitis (FIG. 17). In the cohort randomized to dermatology, using this temperature threshold to diagnosis cellulitis confers a sensitivity of 96.6%, specificity of 45.5%, positive predictive value (PPV) of 82.4%, negative predictive value (NPV) of 83.3%, and accuracy of 82.5% (FIG. 23 and FIG. 24).

Another model predicted cellulitis by temperature gradient as a percentage of the unaffected skin temperature. Using a threshold temperature difference of 1.35% of the affected skin temperature produced analogous results to Model 1 (FIG. 25 and FIG. 26). Both classification models have corresponding formulas which predict the probability of cellulitis diagnosis based on a patient's temperature gradient (FIG. 26). The cohort randomized to standard of care was used to validate Model 1. As such, using a temperature gradient of ≥0.47° C. as predictive of cellulitis, 100% of cellulitis cases (24/24) and 50% (4/8) of pseudocellulitis cases were correctly identified (FIG. 23 and FIG. 24). The model exhibited a PPV of 85.7%, NPV of 100%, and accuracy of 87.5%.

This study evaluated the use of objective skin surface temperature measurements to differentiate cellulitis from pseudocellulitis. Previous literature demonstrates a misdiagnosis rate of over 30% in patients with presumed cellulitis. Cellulitis misdiagnosis comes at significant cost to the healthcare system including overuse of antibiotics, unnecessary hospitalizations, and complications from inappropriate treatment. The cost of admission for misdiagnosed lower limb cellulitis alone is estimated at $195 million to $515 million in avoidable healthcare spending annually. Because involvement of dermatologists and infectious disease physicians has been shown to improve diagnostic accuracy and treatment, some consider the gold standard of cellulitis diagnosis to be recognition by these specialists, however the majority of cellulitis cases are seen and managed exclusively by primary care, emergency medicine or internal medicine physicians. This study offers a low cost, point of care, objective data point that may augment clinical decision making and potentially decrease the misdiagnosis rate.

These results indicate that not only is the affected skin temperature in cellulitis significantly higher than in pseudocellulitis (34.1 vs. 31.5° C., p=0.008), but also that the temperature gradient between affected and unaffected sites in patients with cellulitis is significantly higher than in patients with pseudocellulitis (3.5° C., 95% CI 1.9-5.2, p=0.002). The ROC curve and high AUC (0.857) of the dermatology consultation cohort further suggests that skin surface temperature difference is a useful test in predicting cellulitis.

Logistic regression was utilized on this cohort to develop a classification model to predict cellulitis. Using the temperature gradient between affected and unaffected skin of ≥0.47° C., 100% of cellulitis patients and 50% of pseudocellulitis patients could be accurately diagnosed within the standard of care cohort. This temperature gradient was chosen because it occurs at a natural inflection point at which cellulitis becomes the more likely diagnosis (i.e. probability equals 50%). Though imperfect, this threshold was chosen because of its high sensitivity (96.6%), as treating true cellulitis with antibiotics is a clinical priority and is perhaps more pertinent than identifying every case of pseudocellulitis. Given the test's specificity, we recognize that clinicians would still be treating approximately 50% of pseudocellulitis inappropriately with antibiotics, however, misdiagnosis would be reduced from the current 100%.

The 40 patients randomized to dermatology consultation were found to have pseudocellulitis at a rate of 28%, which aligns with findings in previous studies estimating misdiagnosis at 30%. In theory, employing this model of thermal imaging would halve that rate. Thus, these data suggest that in patients with temperature gradients of <0.47° C., alternative diagnoses should be investigated and clinicians should consider withholding antibiotics. It is anticipated that thermal imaging would be utilized along with other clinical and laboratory factors to further improve diagnostic accuracy.

The present disclosure demonstrates that skin temperature thresholds offer the ability to differentiate these clinical entities and therefore potentially decrease misdiagnosis of cellulitis. This is particularly pertinent since primary care and urgent care physicians, rather than dermatologists or infectious disease specialists, may be more often called upon to diagnose SSTIs and may benefit from a concrete, point-of-care data point to supplement their clinical intuition.

Cellulitis is costly, and studies suggest that its prevalence has increased in the past two decades. The results of this study indicate that skin surface temperature via thermal imaging is a useful metric in differentiating cellulitis from pseudocellulitis. Thermal imaging for the diagnosis of cellulitis has the potential to improve patient care, decrease healthcare cost, and facilitate antibiotic stewardship.

The present disclosure has described one or more preferred embodiments, and it should be appreciated that many equivalents, alternatives, variations, and modifications, aside from those expressly stated, are possible and within the scope of the invention.

The invention claimed is:

1. A diagnostic system comprising:
   a spectrometer system configured to irradiate a soft tissue within a region of interest of a subject, and configured to generate spectral data by acquiring at least a portion of reflected or emitted light from the region of interest;
   a thermal detection system comprising at least one thermal sensor that is configured to acquire thermal detection data from the region of interest;
   a computer system communicatively coupled to the thermal detection system and the spectrometer system, and wherein the computer system is programmed to:
   control the spectrometer system to generate the spectral data by irradiating the region of interest at one or more wavelength, and acquiring the at least a portion of reflected or emitted light from the region of interest;
   control the thermal detection system to acquire the thermal detection data from the region of interest using the at least one thermal sensor;
   utilize one or more parameters from the thermal detection data and the spectral data in a classification model that classifies the soft tissue in the region of interest as corresponding to a soft tissue infection;
   generate a report that includes a classification of the soft tissue infection or a plurality of parameters indicative of the soft tissue infection; and
   wherein the soft tissue comprises skin and wherein the computer system is further programmed to utilize the one or more parameters from the thermal detection data and the spectral data in the classification model to identify and differentiate between cellulitis and pseudocellulitis, and wherein the classification of the soft tissue infection in the generated report includes at least one of a classification of the identified cellulitis or the identified pseudocellulitis or a plurality of parameters indicative of the identified cellulitis or the identified pseudocellulitis.

2. The diagnostic system of claim 1 wherein computer system comprises a mobile device that includes at least one of a phone, a tablet, or a portable computer.

3. The diagnostic system of claim 2 wherein the thermal detection system and the spectrometer system are configured to form a mobile device attachment that is adapted to receive and become communicatively coupled to the mobile device.

4. The diagnostic system of claim 1 wherein the computer system is further programmed to generate the one or more parameters from the spectral data to utilize in the classification model, wherein the one or more parameters is selected from a spectral ratio, a blood oxygenation level, and a capillary refill time.

5. The diagnostic system of claim 4 wherein the computer system is further programmed to calculate the blood oxygenation level from the spectral data by calculating a spectral ratio between a deoxyhemoglobin peak and an oxyhemoglobin peak.

6. The diagnostic system of claim 4 wherein the computer system is further programmed to calculate a deoxyhemoglobin peak at a spectral absorption of 556 nm and an oxyhemoglobin peak at a spectral absorption of 549 nm.

7. The diagnostic system of claim 1 wherein the computer system is further programmed to control the thermal detection system to acquire thermal detection data using the at least one thermal sensor from an affected region and an unaffected region.

8. The diagnostic system of claim 7 wherein the computer system is further programmed to generate the one or more parameters from the thermal detection data to utilize in the classification model, wherein the one or more parameters is selected from a temperature difference between the affected region and the unaffected region, and a temperature ratio between the affected region and the unaffected region.

9. The diagnostic system of claim 8 wherein the computer system is further programmed to generate the temperature difference between a maximum temperature in the affected region and a temperature in the unaffected region.

10. The diagnostic system of claim 8 wherein the computer system is further programmed to generate the temperature ratio by taking the temperature difference between the affected region and the unaffected region and dividing the temperature difference by a temperature in the unaffected region.

11. The diagnostic system of claim 8 wherein the unaffected region of interest is located on an ipsilateral region or a contralateral region of the subject.

12. The diagnostic system of claim 1 wherein the computer system is further programmed to fit the classification model to the one or more parameters from the thermal detection data and the spectral data to generate a classification threshold, wherein the classification threshold is used to identify and differentiate between the cellulitis and pseudocellulitis.

13. The diagnostic system of claim 1 wherein the classification model comprises a linear classifier.

14. The diagnostic system of claim 13 wherein the computer system is further programmed to fit the linear classifier using a blood oxygenation level from the spectral data and a temperature difference from the thermal detection data to generate a classifier slope and a classifier intercept and wherein the classifier slope and classifier intercept are utilized to determine a classification threshold.

15. The diagnostic system of claim 1 wherein the computer system is further programmed to control the spectrometer system to irradiate the soft tissue using at least one illumination fiber in a fiber optic probe, and to acquire the reflected or emitted light using at least one detection fiber in the fiber optic probe to generate the spectral data.

16. A diagnostic system comprising:
a spectrometer system comprising a light source configured to irradiate a soft tissue within a region of interest of a subject, and a detector configured to acquire at least a portion of light that is reflected or emitted from the region of interest;
a computer system communicatively coupled to the spectrometer system, and wherein the computer system is programmed to:
control the spectrometer system to generate spectral data by irradiating the region of interest at one or more wavelength, and acquiring the at least a portion of the light that is reflected or emitted from the region of interest;
utilize one or more parameters from the spectral data in a classification model that classifies the soft tissue in the region of interest as corresponding to a soft tissue infection;
generate a report that includes a classification of the soft tissue infection; and
wherein the soft tissue comprises skin and wherein the computer system is further programmed to utilize the one or more parameters from the spectral data in the classification model to identify and differentiate between cellulitis and pseudocellulitis, and wherein the classification of the soft tissue infection in the generated report includes at least one of a classification of the identified cellulitis or the identified pseudocellulitis or a plurality of parameters indicative of the identified cellulitis or the identified pseudocellulitis.

17. The diagnostic system of claim 16 wherein the computer system is further programmed to generate the one or more parameters from the spectral data to utilize in the classification model, wherein the one or more parameters is selected from a spectral ratio, a blood oxygenation level, and a capillary refill time.

18. The diagnostic system of claim 17 wherein the computer system is further programmed to calculate the blood oxygenation level from the spectral data by calculating a spectral ratio between a deoxyhemoglobin peak and an oxyhemoglobin peak.

19. A diagnostic system comprising:
a thermal detection system comprising at least one thermal sensor that is configured to acquire thermal detection data from a region of interest of a soft tissue of a subject;
a computer system communicatively coupled to the thermal detection system, and wherein the computer system is programmed to:
control the thermal detection system to acquire the thermal detection data from the region of interest using the at least one thermal sensor; and
utilize one or more parameters from the thermal detection data in a classification model that classifies the soft tissue in the region of interest as corresponding to a soft tissue infection;
generate a report that includes a classification of the soft tissue infection; and
wherein the soft tissue comprises skin and wherein the computer system is further programmed to utilize the one or more parameters from the thermal detection data in the classification model to identify and differentiate between cellulitis and pseudocellulitis, and wherein the classification of the soft tissue infection in the generated report includes at least one of a classification of the identified cellulitis or the identified pseudocellulitis or a plurality of parameters indicative of the identified cellulitis or the identified pseudocellulitis.

* * * * *

UNITED STATES PATENT AND TRADEMARK OFFICE
CERTIFICATE OF CORRECTION

PATENT NO. : 11,452,479 B2
APPLICATION NO. : 16/500462
DATED : September 27, 2022
INVENTOR(S) : Richard R. Anderson et al.

It is certified that error appears in the above-identified patent and that said Letters Patent is hereby corrected as shown below:

In the Specification

Column 13, Line 30, "$\geq 1.8$ years" should be --$\geq 18$ years--.

Column 20, Line 25, "of 0.47°" should be --of $\geq 0.47°$--.

Signed and Sealed this
Seventh Day of February, 2023

Katherine Kelly Vidal
*Director of the United States Patent and Trademark Office*